(12) United States Patent
Abdel-Naby et al.

(10) Patent No.: US 10,953,132 B2
(45) Date of Patent: *Mar. 23, 2021

(54) METHOD TO ENHANCE WOUND HEALING USING SILK-DERIVED PROTEIN

(71) Applicants: Cornell University, Ithaca, NY (US); Silk Technologies, Ltd., Plymouth, MN (US)

(72) Inventors: Waleed Abdel-Naby, Brooklyn, NY (US); Mark Rosenblatt, Ithaca, NY (US); Brian D. Lawrence, Tampa, FL (US); David W. Infanger, Maple Grove, MN (US)

(73) Assignees: Cornell University, Ithaca, NY (US); Silk Technologies, Ltd., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/091,482

(22) PCT Filed: Apr. 7, 2017

(86) PCT No.: PCT/US2017/026656
§ 371 (c)(1),
(2) Date: Oct. 4, 2018

(87) PCT Pub. No.: WO2017/200659
PCT Pub. Date: Nov. 23, 2017

(65) Prior Publication Data
US 2019/0117834 A1    Apr. 25, 2019

Related U.S. Application Data

(60) Provisional application No. 62/320,177, filed on Apr. 8, 2016.

(51) Int. Cl.
| | |
|---|---|
| *A21D 13/064* | (2017.01) |
| *A61L 27/22* | (2006.01) |
| *A61K 9/00* | (2006.01) |
| *A61L 27/36* | (2006.01) |
| *A61P 27/02* | (2006.01) |
| *A61P 17/02* | (2006.01) |
| *A61K 38/17* | (2006.01) |

(52) U.S. Cl.
CPC .......... *A61L 27/227* (2013.01); *A61K 9/0048* (2013.01); *A61K 38/1767* (2013.01); *A61L 27/3604* (2013.01); *A61P 17/02* (2018.01); *A61P 27/02* (2018.01); *A61K 9/0014* (2013.01); *A61L 2430/16* (2013.01)

(58) Field of Classification Search
None
See application file for complete search history.

(56) References Cited

U.S. PATENT DOCUMENTS

| | | |
|---|---|---|
| 5,591,426 A | 1/1997 | Dabrowski et al. |
| 5,895,645 A | 4/1999 | Dabrowski et al. |
| 6,034,220 A | 3/2000 | Stedronsky |
| 6,280,747 B1 | 8/2001 | Philippe et al. |
| 7,060,260 B2 | 6/2006 | Fahnestock et al. |
| 7,115,388 B2 | 10/2006 | Tsubouchi |
| 7,193,038 B2 | 3/2007 | Tsubouchi et al. |
| 7,635,755 B2 | 12/2009 | Kaplan et al. |
| 8,097,583 B2 | 1/2012 | Scheibel et al. |
| 8,361,617 B2 | 1/2013 | Kaplan et al. |
| 8,420,077 B2 | 4/2013 | Altman et al. |
| 8,481,681 B2 | 7/2013 | Sutherland et al. |
| 8,496,976 B2 | 7/2013 | Gore et al. |
| 8,614,293 B2 | 12/2013 | Kaplan et al. |
| 8,742,069 B2 | 6/2014 | Kaplan et al. |
| 9,394,355 B2 * | 7/2016 | Lawrence ................. A23L 2/66 |
| 2003/0206897 A1 | 11/2003 | Trani et al. |
| 2004/0219630 A1 | 11/2004 | Tsubouchi |
| 2004/0265062 A1 | 12/2004 | Tsubouchi et al. |
| 2005/0143296 A1 | 6/2005 | Tsubouchi et al. |
| 2005/0196370 A1 | 9/2005 | Yu et al. |
| 2005/0202097 A1 | 9/2005 | Maskin |
| 2006/0106104 A1 | 5/2006 | Vehige et al. |
| 2008/0219938 A1 | 9/2008 | Grune |
| 2009/0234026 A1 | 9/2009 | Kaplan et al. |
| 2011/0008406 A1 | 1/2011 | Altman et al. |
| 2011/0105402 A1 | 5/2011 | Kim et al. |
| 2012/0052124 A1 | 3/2012 | Kaplan et al. |

(Continued)

FOREIGN PATENT DOCUMENTS

| | | |
|---|---|---|
| CN | 101194666 A | 6/2008 |
| CN | 102860969 A | 1/2013 |

(Continued)

OTHER PUBLICATIONS

Chutipakdeevong, J. Appl. Polym. Sci. 130: 3634-3644, 2013 (Year: 2013).*
Wu, Adv Mater Res.; 311 -313; 1755-1759; Aug. 2011 (Year: 2011).*
Liu, Invest Ophthalmol Vis Sci. 2012;53:4130-4138. (Year: 2012).*
Asakura et al., "Possible Implications of Serine and Tyrosine Residues and Intermolecular Interactions on the Appearance of Silk I Structure of Bombyx Mori Silk Fibroin-Derived Synthetic Peptides: High-Resolution 13C Cross-Polarization/Magic-Angle Spinning NMR Study," Biomacromolecules, 6(1):468-474, Jan.-Feb. 2005.

(Continued)

*Primary Examiner* — Satyanarayana R Gudibande
(74) *Attorney, Agent, or Firm* — Haukaas Fortius PLLC; Michael H. Haukaas

(57) ABSTRACT

Described herein are methods of enhancing wound healing using silk-derived proteins (SDP), including low molecular weight SDP fragments. Also described are compositions for the treatment of wounds, including corneal wounds, skin wounds, surgical incisions, burns, and skin ulcers, comprising SDP fragments, including low molecular weight SDP fragments.

12 Claims, 13 Drawing Sheets

Specification includes a Sequence Listing.

(56) References Cited

U.S. PATENT DOCUMENTS

| | | |
|---|---|---|
| 2012/0171256 A1 | 7/2012 | Zhang et al. |
| 2013/0039986 A1 | 2/2013 | Kaplan et al. |
| 2013/0158131 A1 | 6/2013 | Kaplan et al. |
| 2013/0165004 A1 | 6/2013 | Kaplan et al. |
| 2013/0243693 A1 | 9/2013 | Omenetto et al. |
| 2013/0243709 A1 | 9/2013 | Hanson et al. |
| 2014/0193466 A1 | 7/2014 | Lawrence et al. |
| 2014/0235554 A1 | 8/2014 | Lawrence et al. |
| 2015/0093340 A1 | 4/2015 | Altman et al. |
| 2016/0096878 A1 | 4/2016 | Lawrence et al. |

FOREIGN PATENT DOCUMENTS

| | | |
|---|---|---|
| CN | 103239707 A | 8/2013 |
| JP | S55124793 A | 9/1980 |
| JP | 0767686 A | 3/1995 |
| JP | H08295697 A | 11/1996 |
| JP | 2000143472 A | 5/2000 |
| WO | 1999033899 A1 | 7/1999 |
| WO | 2007130364 A2 | 11/2007 |
| WO | 2009088119 A1 | 7/2009 |
| WO | 2012170655 A1 | 12/2012 |
| WO | 2013126799 A1 | 8/2013 |
| WO | 2013159101 A1 | 10/2013 |
| WO | 2014145002 A2 | 9/2014 |
| WO | 2014152097 A1 | 9/2014 |
| WO | 2015077300 A1 | 5/2015 |
| WO | 2017200659 A2 | 11/2017 |

OTHER PUBLICATIONS

Daithankar et al., "Moisturizing Efficiency of Silk Protein Hydrolysate: Silk Fibroin," Indian J. Biotech., 4:115-121, Jan. 2005.

Extended Search Report of the European Patent Office dated Apr. 24, 2018 in EP Application No. 15833824.4.6 (EP3182985A1), 7pgs.

Greving et al., "Shear-Induced Self-Assembly of Native Silk Proteins into Fibrils Studied by Atomic Force Microscopy," Biomacromolecules, 13(3):676-682, Feb. 2012.

Hardy et al., "Polymeric Materials Based on Silk Proteins," Polymer, 49(20):4309-4327, Sep. 2008.

Harkin et al., "Silk Fibroin in Ocular Tissue Reconstruction," Biomaterials, 32(10):2445-58, Apr. 2011.

International Search Report and Written Opinion of the ISA/US dated Dec. 14, 2015 in International Application No. PCT/US2015/046141, 17pgs.

International Search Report and Written Opinion of the ISA/US dated Dec. 22, 2017 in International Application No. PCT/US2017/026656, 12pgs.

Kang et al., "Preparation and Characterization of Low Molecular Weight Silk Fibroin by High-Temperature and High Pressure Method," J. Applied Polymer Sci., 85(14):2890-2895, Sep. 2002.

Kaur et al., "Photoprotection by Silk Cocoons," Biomacromolecules, 14(10):3660-3667, Sep. 2013.

Matsumoto et al., "Mechanisms of Silk Fibroin Sol-Gel Transitions," J Phys Chem B., 110(43):21630-2638, Nov. 2008.

Patchornik et al., "Nonenzymatic Cleavages of Peptide Chains at the Cysteine and Serine Residues Through Their Conversion Into Dehydroalanine. I. Hydrolytic and Oxidative Cleavage of Dehydroalanine Residues," J. Am. Chem. Soc., 86(6):1206-1212, Mar. 1964.

Rockwood et al., "Materials Fabrication from Bombyx mori Silk Fibroin," Nat Protoc., 6(10):1612-1631, Sep. 2011.

Teng et al., "Physical Crosslinking Modulates Sustained Drug Release from Recombinant Silk-Elastinlike Protein Polymer for Ophthalmic Applications," J. Control Release, 156(2):186-197, Dec. 2011.

Wang et al., "Sonication-Induced Gelation of Silk Fibroin for Cell Encapsulation," Biomaterials, 29(8):1054-1064, Apr. 2008.

Wu et al., "Impact of Sterilization Methods on the Stability of Silk Fibroin Solution," Adv Mater Res.; 311-313:1755-1759; Aug. 2011.

Yamada et al., "Preparation of Undegraded Native Molecular Fibroin Solution from Silkworm Cocoons," Mater Sci Eng.: C; 14(1-2):41-46; Aug. 2001.

Zhao et al., "The Effects of Different Sterilization Methods on Silk Fibroin," J Biomedical Science and Engineering, 4:397-402, May 2011.

\* cited by examiner

Fig. 4A-B

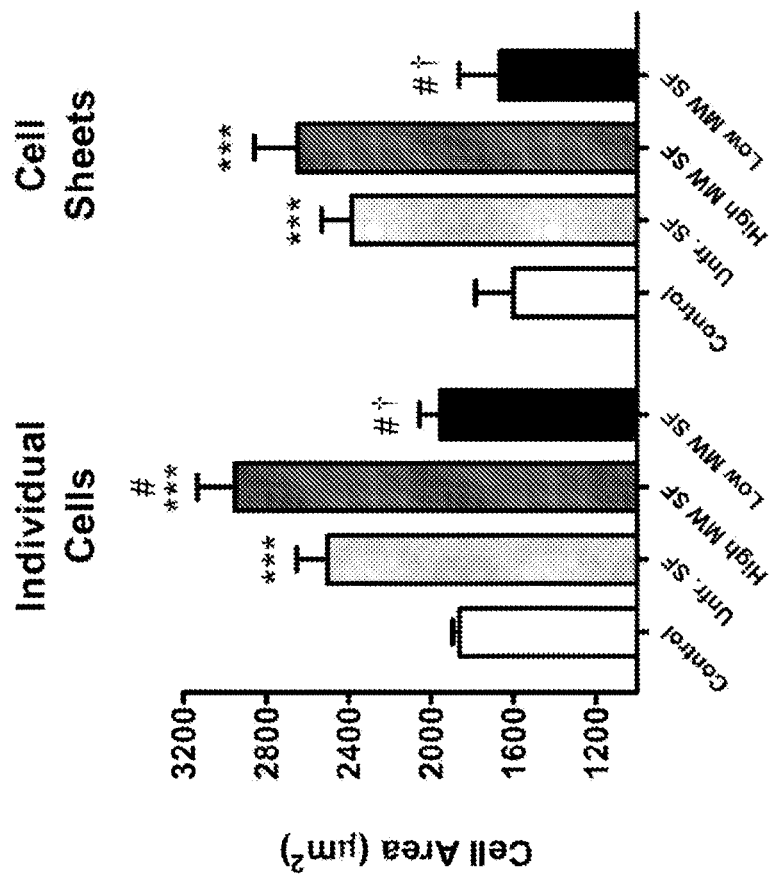
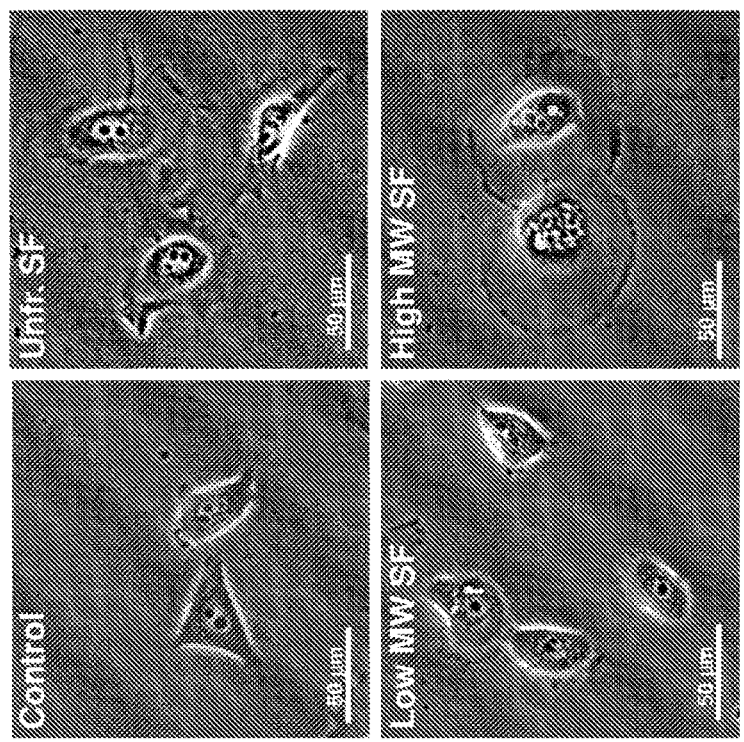
Fig. 11A
Fig. 11B

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttttggtgca ggaggacaag                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcacacatgt gatgataagg                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aatggtggaa acccacaacg                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctgctccac ttttaacttg                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                                        -continued
         primer

<400> SEQUENCE: 5
gttcagagtc tttcgtttgc                                                      20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcagttacat cgaaggagag                                                      20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgagcacat tgccaaacag                                                      20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggacagtgaa tgctgatttc                                                      20

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Gly Ala
1
```

METHOD TO ENHANCE WOUND HEALING USING SILK-DERIVED PROTEIN

PRIORITY

This application is a National Stage filing under 35 U.S.C. § 371 of International Application No. PCT/US2017/026656, filed Apr. 7, 2017, which claims priority under 35 U.S.C. § 119(e) to U.S. Provisional Patent Application No. 62/320,177, filed Apr. 8, 2016, the contents of which applications are incorporated herein by reference in their entirety.

STATEMENT OF FEDERAL FUNDING

This invention was made with government support under Grant No. DGE-1144153 and Grant No. 1152561 awarded by National Science Foundation, and Grant No. A151-061-0107 awarded by the US Army. The government has certain rights in the invention.

SEQUENCE LISTING

The instant application contains a Sequence Listing which has been submitted electronically in ASCII format and is hereby incorporated by reference in its entirety. The ASCII copy, created on Oct. 3, 2018, is named 114013US1_SL.txt and is 2250 bytes in size.

BACKGROUND OF THE INVENTION

Corneal epithelial wound healing relies on a complex and dynamic repair process directed to the regeneration and remodeling of the corneal epithelium and is essential for the proper restoration of the cornea's highly regular and organized tissue architecture, as well as maintenance of its ocular integrity and transparency to ensure normal vision for the eye. Following injury, re-epithelialization of corneal defects involves the collective migration of properly adherent basal epithelial cell sheets to cover the wounded surface, followed by an increase in epithelial cell proliferation and differentiation to repopulate the denuded area and restore a nonkeratinized stratified epithelium. Integration of key epithelial cell behaviors throughout the wound healing process, including migration, proliferation, cytoskeletal re-organization, and adhesion, is driven by an organized cascade of signaling events, stimulated by the release of various growth factors and cytokines into the injury site, and is essential to the efficient and effective repair of the ocular surface. Severe traumatic injuries, however, can render the naturally occurring regenerative properties of the cornea incapable of restoring a healthy epithelial surface and thus unable to reconstitute its critical barrier function. Thus, there is a need for novel biomaterials and therapies to promote the acceleration of wound healing and alleviate the complications of improper corneal epithelial regeneration.

SUMMARY

Described herein are methods of enhancing wound healing using Silk-derived Proteins (SDPs), including low molecular weight SDPs. Also described are compositions for the treatment of wounds, including corneal wounds and skin wounds, or scars comprising SDPs, including low molecular weight SDPs. In some embodiments, the compositions provided herein are effective to promote wound healing.

Described herein, in certain embodiments, are methods for treating a wound comprising administering to a subject in need thereof a composition comprising low molecular weight SDP. In some embodiments, methods for treating a wound or a scar are provided herein. In some embodiments, the methods provided herein comprise applying a composition of Silk-derived Protein (SDP) fragments to living animal tissue in a wound. In some embodiments, the composition is topically applied to corneal wounds or skin wounds, covering the outer surface of the wound. In some embodiments, the SDP fragments have primary amino acid sequences that differ from native fibroin by at least 4% with respect to the combined amino acid content of serine, glycine, and alanine. In some embodiments, a plurality of the SDP fragments terminate in amide ($-C(=O)NH_2$) groups. Compositions provided herein have, in some embodiments, a serine content that is reduced by greater than 40% compared to native fibroin, wherein the serine content is at least about 5%. In some embodiments, the cysteine disulfide bonds between the fibroin heavy and fibroin light protein chains of fibroin are reduced or eliminated. Compositions provided herein possess in some embodiments enhanced stability in an aqueous solution. In some embodiments, the SDP fragments are derived from silkworm silk, spider silk, or genetically engineered silk. In some embodiments, the SDP fragments are derived from *Bombyx mori*.

Compositions provided herein, in certain embodiments, have an average molecular weight between about 30 kDa and 60 kDa. In some embodiments, at least 75 percent of the SDP fragments have a molecular weight of less than about 100 kDa. In some embodiments, the SDP fragments have a molecular weight of less than about 100 kDa to promote cell migration and proliferation in the tissue to close the wound. In some embodiments, at least 90 percent of the SDP fragments have a molecular weight of less than about 100 kDa. In some embodiments, at least 75 percent of the SDP fragments have a molecular weight of less than about 80 kDa. In some embodiments, at least 90 percent of the SDP fragments have a molecular weight of less than about 80 kDa. In some embodiments, at least 75 percent of the SDP fragments have a molecular weight of less than about 60 kDa. In some embodiments, the SDP fragments have a molecular weight of less than about 60 kDa to promote cell migration and proliferation in the tissue to close the wound. In some embodiments, at least 90 percent of the SDP fragments have a molecular weight of less than about 60 kDa to promote cell migration and proliferation in the tissue to close the wound. In some embodiments, at least 75 percent of the SDP fragments have a molecular weight of less than about 50 kDa. In some embodiments, at least 90 percent of the SDP fragments have a molecular weight of less than about 50 kDa. In some embodiments, at least 75 percent of the SDP fragments have a molecular weight between about 30 kDa and 60 kDa. In some embodiments, at least 90 percent of the SDP fragments have a molecular weight between about 30 kDa and 60 kDa. In some embodiments, at least 75 percent of the SDP fragments have a molecular weight of less than about 30 kDa. In some embodiments, at least 90 percent of the SDP fragments have a molecular weight of less than about 30 kDa. In some embodiments, at least 75 percent of the SDP fragments have a molecular weight of between about 10 kDa and 30 kDa. In some embodiments, at least 90 percent of the SDP fragments have a molecular weight of between about 10 kDa and 30 kDa. In some embodiments, at least 75 percent of the SDP fragments have a molecular weight of less than about 10 kDa. In some embodiments, at least 90 percent of the SDP fragments have a molecular weight of less than about 10 kDa. In some embodiments, at least 50 percent of the SDP fragments have a molecular weight of greater than about 60 kDa. In some cases, SDP fragments increase transforming growth beta factor signaling in cells in the wound.

Wounds for treatment with the compositions provided herein are, in some embodiments, an ocular wound, a surgical wound, an incision, or an abrasion. In some cases, the wound is an ocular wound caused by an ocular condition, such as, corneal ulcer, corneal erosion, corneal abrasion, corneal degeneration, corneal perforation, corneal scarring, epithelial defect, keratoconjunctivitis, idiopathic uveitis, corneal transplantation, dry eye syndrome, age-related macular degeneration, diabetic eye, blepharitis, glaucoma, ocular hypertension, post-operative eye pain and inflammation, posterior segment neovascularization, proliferative vitreoretinopathy, cytomegalovirus retinitis, endophthalmitis, choroidal neovascular membrane, vascular occlusive disease, allergic eye disease, tumor, retinitis pigmentosa, eye infection, scleritis, ptosis, miosis, eye pain, mydriasis, neuralgia, cicatrizing ocular surface disease, ocular infection, inflammatory ocular disease, ocular surface disease, corneal disease, retinal disease, ocular manifestations of systemic diseases, hereditary eye condition, ocular tumor, increased intraocular pressure, herpetic infection, ptyrigium or scleral tumor, wound sustained to ocular surface, post-photorefractive keratotomy eye pain and inflammation, thermal or chemical burn to the cornea, scleral wound, or keratoconus and conjunctival wound.

Compositions for treating a wound or a scar are provided herein. In some embodiments, such compositions comprise SDP fragments having primary amino acid sequences that differ from native fibroin by at least 4% with respect to the combined amino acid content of serine, glycine, and alanine. In some embodiments, a plurality of the SDP fragments terminate in amide (—C(=O)NH$_2$) groups. In some embodiments, the compositions provided herein comprise SDP fragments that have a serine content that is reduced by greater than 40% compared to native fibroin, wherein the serine content is at least about 5%. In some embodiments, at least 75 percent of the SDP fragments have a molecular weight of less than about 100 kDa to promote cell migration and proliferation in the tissue to close the wound. In some embodiments, the compositions provided herein comprise a pharmaceutical carrier. In some embodiments, the pharmaceutical carrier is phosphate buffered saline, a film, a fiber, a foam, a hydrogel, a matrix, a three-dimensional scaffold, a microparticle, a nanoparticle, a polymer, or a mat. In some embodiments, the SDP fragments are attached to a substrate. In some embodiments, the substrate is a corneal transplant, a wound dressing, a contact lens, a tissue, a tissue-graft, or a degradable material.

Methods of making compositions for treating wounds are provided herein. In some embodiments, the methods comprise separating a second composition of SDP fragments from a first composition of SDP fragments. In some embodiments, SDP fragments in the second composition have a lower average molecular weight than the SDP fragments in the first composition. In some embodiments, the SDP fragments in the first composition have primary amino acid sequences that differ from native fibroin by at least 4% with respect to the combined amino acid content of serine, glycine, and alanine. In some embodiments, a plurality of the SDP fragments in the first composition terminates in amide (—C(=O)NH$_2$) groups. In some embodiments, the SDP fragments in the first composition have a serine content that is reduced by greater than 40% compared to native fibroin. In some embodiments, the serine content is at least about 5%. In some embodiments, at least 75 percent of the SDP fragments in the second composition have a molecular weight of less than about 100 kDa to promote cell migration and proliferation in the tissue to close the wound. In some embodiments, the second composition is separated from the first composition by centrifuge. In some embodiments, the first composition is prepared by a process comprising heating an aqueous fibroin solution at an elevated pressure. In some embodiments, the aqueous fibroin solution comprises lithium bromide at a concentration of at least 8M. In some embodiments, the aqueous fibroin solution is heated to at least about 105° C. (221° F.) under a pressure of at least about 10 PSI for at least about 20 minutes to provide the first composition. In some embodiments, the first composition comprises less than 8.5% serine amino acid residues, and the first composition has an aqueous viscosity of less than 5 cP as a 10% w/w solution in water.

In some embodiments, the low molecular weight SDP is less than 100 kDa. In some embodiments, the low molecular weight SDP is less than 80 kDa. In some embodiments, the low molecular weight SDP is 10%, 20%, 30%, 40%, 50%, 60%, 70%, 80%, 90% or greater of the total SDP in the composition. In some embodiments, the composition does not comprise high molecular weight SDP. In some embodiments, the low molecular weight SDP is derived from silkworm silk, spider silk or genetically engineered silk. In some embodiments, the low molecular weight SDP is derived from *Bombyx mori*. In some embodiments, the wound is an ocular wound, a surgical wound, an incision, or an abrasion. In some embodiments, the wound is a corneal wound. In some embodiments, the subject has an ocular condition. In some embodiments, the ocular condition is selected from among the groups consisting of a corneal ulcer, corneal erosion, corneal abrasion, corneal degeneration, corneal perforation, corneal scarring, an epithelial defect, keratoconjunctivitis, idiopathic uveitis, corneal transplantation, dry eye syndrome, age-related macular degeneration (AMD, wet or dry), diabetic eye conditions, blepharitis, glaucoma, ocular hypertension, post-operative eye pain and inflammation, posterior segment neovascularization (PSNV), proliferative vitreoretinopathy (PVR), cytomegalovirus retinitis (CMV), endophthalmitis, choroidal neovascular membranes (CNVM), vascular occlusive diseases, allergic eye disease, tumors, retinitis pigmentosa, eye infections, scleritis, ptosis, miosis, eye pain, mydriasis, neuralgia, cicatrizing ocular surface diseases, ocular infections, inflammatory ocular diseases, ocular surface diseases, corneal diseases, retinal diseases, ocular manifestations of systemic diseases, hereditary eye conditions, ocular tumors, increased intraocular pressure, herpetic infections, ptyrigium (scleral tumor), wounds sustained to ocular surface, post-photorefractive keratotomy eye pain and inflammation, thermal or chemical burns to the cornea, scleral wounds, keratoconus and conjunctival wounds. In some embodiments, the ocular condition is caused by aging, an autoimmune condition, trauma, infection, a degenerative disorder, endothelial dystrophies, and/or a surgery.

Described herein, in certain embodiments, are compositions comprising low molecular weight SDP and a pharmaceutically acceptable carrier. In some embodiments, the low molecular weight SDP is less than 100 kDa. In some embodiments, the low molecular weight SDP is less than 80 kDa. In some embodiments, the carrier is phosphate buffered saline. In some embodiments, the low molecular weight SDP is 10%, 20%, 30%, 40%, 50%, 60%, 70%, 80%, 90% or greater of the total SDP in the composition. In some embodiments, the composition does not comprise high molecular weight SDP. In some embodiments, the low molecular weight SDP is derived from silkworm silk, spider silk or genetically engineered silk. In some embodiments, the low molecular weight SDP is derived from *Bombyx mori*. In some embodiments, the carrier is a film, a fiber, a foam, a hydrogel, a matrix, a mesh, a three-dimensional scaffold, a microparticle, a nanoparticle a polymer or a mat. In some embodiments, the low molecular weight SDP is attached to a substrate. In some embodiments, the substrate is a corneal transplant. In some embodiments, the substrate is a wound dressing or a contact lens. In some embodiments, the substrate is a tissue graft. In some embodiments, the substrate degrades following administration to a subject.

Compositions comprising low molecular weight SDP fragments or high molecular weight SDP fragments or combinations thereof are provided herein. Low molecular weight SDP fragments can increase cell proliferation, migration, and wound closure rate. In some embodiments, the low molecular weight SDP fragments are used in treating inflamed wounds. In some cases, in some embodiments, it is useful to apply a composition of low molecular weight SDP fragments to speed up wound healing. In some embodiments, these cases include wounds acquired on the battlefield during war, surgical wounds on a relatively healthy person who desires quick healing for pain relief or wounds acquired in a high infection area. High molecular weight SDP fragments can increase cell adhesion to the basement membrane or aid in basement membrane formation. In some cases, it is useful to apply a composition of high molecular weight SDP fragments for chronic wounds or wounds that fester or wounds that have difficulty healing up, such as diabetic ulcers or skin burns. Where low molecular weight SDP fragments are involved in wound closure rate, high molecular weight SDP fragments can be involved in wound closure quality. In some cases, a composition of selected low molecular weight SDP fragments and high molecular weight SDP fragments is applied for optimal wound healing rate and quality.

BRIEF DESCRIPTION OF THE DRAWINGS

FIG. 8A are representative images from wound healing assay demonstrate that cell growth and migration into the cell-free region (outlined in white) is significantly accelerated in the presence of low molecular weight SDP. FIG. 8B is a summary bar graph illustrating percent wound closure at indicated time points during the scratch wound assay (*** $p<0.05$ vs. Control; #$p<0.05$ vs. Unfr. SF; † $p<0.05$ vs. High MW SF; N=3, n=3).

FIG. 11A illustrates a representative phase contrast images demonstrate an increase in HCLE cell spreading in the presence of high MW SDP. FIG. 11B are summary graphs represent mean surface area of HCLE cells cultured sparsely (individual cells) or to confluence (cell sheets), in the presence of different MW SDP solutions, or PBS treatment vehicle (control) (*** $p<0.05$ vs. Control; #$p<0.05$ vs. Unfr. SF; † $p<0.05$ vs. High MW SF; N=3, n=100).

FIG. 13A representative images from scratch wound healing assay. FIG. 13B is a summary bar graph illustrating percent wound closure at indicated time points during the scratch wound healing assay (*** $p<0.05$ vs. Control; † $p<0.05$ vs. Low MW SF; # $p<0.05$ vs. Control (+SB431542); N=3, n=3).

DETAILED DESCRIPTION OF THE INVENTION

Figure 1:
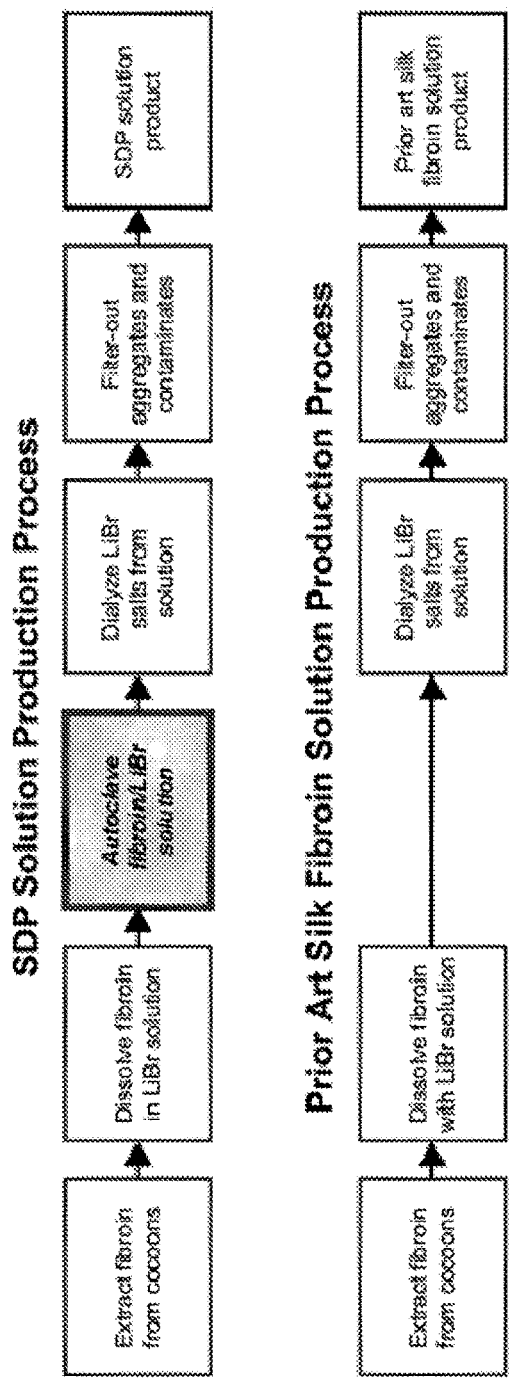
FIG. 1 shows a flowchart illustrating key processing steps for the generation of both SDP solution and Prior Art Silk Fibroin (PASF) solution. The SDP Production Process contains an additional step (italicized in center) to enhance solution stability over time, which is not performed during the PASF solution production process.

Protein compositions derived from SDP for treating wounds are provided herein. In some cases, SDP compositions provided herein can include or be derived from the protein compositions described in U.S. Patent Publication No. 2016/0096878, the entire disclosure of which is hereby incorporated by reference into this specification. SDP compositions provided herein can possesses enhanced solubility and stability in aqueous solutions. Methods of making SDP compositions provided herein can include modifying the primary amino acid sequence of native fibroin such that cysteine disulfide bonds between the fibroin heavy and fibroin light protein chains are reduced or eliminated. Additionally, SDP compositions provided herein can have a serine content that is reduced by greater than 40% compared to native fibroin protein and the average molecular weight of the proteins being less than about 100 kDa. In some embodiments, the SDP compositions provided herein are employed for the treatment of wounds, including, but not limited to corneal wounds, skin wounds, surgical incisions, burns, or skin ulcers (e.g., diabetic skin ulcers).

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described can include a particular aspect, feature, structure, moiety, or characteristic, but not every embodiment necessarily includes that aspect, feature, structure, moiety, or characteristic. Moreover, such phrases can, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a component" includes a plurality of such components, so that a component X includes a plurality of components X. It is further noted that the claims can be drafted to exclude an optional element. As such, this statement is intended to serve as antecedent basis for the use of exclusive terminology, such as "solely," "only," "other than", and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, element, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, an invention encompasses not only the entire group listed as a whole, but each member of the group individually and all possible subgroups of the main group. Additionally, for all purposes, an invention encompasses not only the main group, but also the main group absent one or more of the group members. An invention therefore envisages the explicit exclusion of any one or more of members of a recited group. Accordingly, provisos can apply to any of the disclosed categories or embodiments whereby any one or more of the recited elements, species, or embodiments, can be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

For a therapeutic application, an "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is within the capacity of persons skilled in the art. The term "effective amount" is intended to include an amount of a composition described herein, or an amount of a combination of peptides described herein, e.g., that is effective to treat or prevent a disease or disorder, or to treat the symptoms of the disease or disorder, in a host. Thus, an "effective amount" generally means an amount that provides the desired effect.

For process and preparation applications, an "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, or conditions related to a process described herein, e.g., that is effective to form the desired products in a reaction mixture. Thus, an "effective amount" generally means an amount that provides the recited desired effect.

As used herein, the term "silk fibroin" includes silkworm fibroin and insect or spider silk protein. See e.g., Lucas et al., Adv. Protein Chem. 13, 107 (1958). Any type of silk fibroin may be used. Silk fibroin produced by silkworms, such as *Bombyx mori*, is the most common and represents an earth-friendly, renewable resource. For instance, silk fibroin may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245, 012), and variants thereof, that may be used.

An exemplary silk fibroin is derived from the *Bombyx mori* silkworm cocoon. The protein fibroin includes a heavy chain that is about 350-400 kDa in molecular weight and a light chain that is about 25 kDa in molecular weight, wherein the heavy and light chains are linked together by a disulfide bond. The primary sequences of the heavy and light chains are known in the art. The fibroin protein chains possess hydrophilic N and C terminal domains, and alternating blocks of hydrophobic/hydrophilic amino acid sequences allowing for a mixture of steric and electrostatic interactions with surrounding molecules in solution. At low concentration dilutions (1% or less) the fibroin protein molecule is known to take on an extended protein chain form and not immediately aggregate in solution. The fibroin protein is highly miscible with hydrating molecules such as HA, PEG, glycerin, and CMC, has been found to be highly biocompatible, and integrates or degrades naturally within the body through enzymatic action. Native fibroin, or also referred to here as PASF, is known in the art and has been described by, for example, Daithankar et al. (*Indian J. Biotechnol.* 2005, 4, 115-121).

The terms "silk-derived protein" (SDP) and "fibroin-derived protein" are used interchangeably herein. These materials are prepared by the processes described herein involving heat, pressure, and a high concentration of a heavy salt solution. Therefore 'silk-derived' and 'fibroin-derived' refer to the starting material of the process that modifies the silk fibroin protein to arrive at a protein composition with the structural, chemical and physical properties described herein.

Overview

In the studies described herein, it was successfully demonstrated that the ability of SDP fragments to influence corneal epithelial cell behavior and enhance the biological processes involved in a wound healing response is dependent on the fragment size of the silk protein delivered in solution form. This work evidences that the versatility of silk fibroin as a biomaterial arises from the protein's chemical and molecular attributes, which are known to be heavily influenced by the various processing modalities and regimes that are required for the final silk product formation. An initial step in the preparation of silk fibroin based biomaterials is the extraction of silk fibers from raw silk worm cocoons through a degumming process, which relies on strong denaturants, such as heat and change in pH, to remove the contaminating sericin protein coating from the silk fibers. The purified fibers are then subsequently solubilized using strong chaotropic agents, including concentrated acids, inorganic salts, fluorinated organic solvents, and ionic liquids, to disrupt the strong hydrogen bonds which stabilize the protein crystal structure, and produce what is termed a regenerated silk fibroin solution, from which a variety of material formats can be fabricated. Consequently, disruption of intermolecular hydrogen and or/van der Waals bonds by exposing the silk fibroin protein to harsh denaturing conditions during the degumming and dissolution processes results in the fracturing and degradation of its peptide molecular structure, ultimately impacting the molecular weight distribution of the regenerated silk fibroin solution and leading to significant changes in its bio-functional material properties.

Previous work has been primarily focused on establishing a relationship between the processing induced fragmentation in the silk fibroin protein structure, and changes in biomaterial properties such as mechanical strength, degradation rate, thermal stability, and biocompatibility when silk is used as a film scaffold material.

When added as a supplement to cell culture, low molecular weight SDP stimulated a significant increase in cell migration rate and proliferation. Contrastingly, treatment with high molecular weight SDP significantly inhibited cell mobility, but did not demonstrate any significant effects on cell proliferation and viability. Additionally, the molecular weight dependent differences in SDP's stimulation of corneal epithelial cell behavior, leading to an enhanced wound healing response, was further pronounced in an in vitro epithelial abrasion model used to assess wound closure.

HCLE cells treated with low molecular weight SDP, showed a significant acceleration in rate of wound closure and entirely occupied the wound area faster, when compared to cells treated with high molecular weight silk, which showed a significant decrease in wound closure rate as a result of slower cell migration and growth. These results implicate the significance of protein molecular weight on the bio-functional properties of SDP and its ability to enhance wound healing through stimulation of cell growth and migration.

Corneal epithelial wound healing requires the integration of key biological processes and epithelial cell behaviors, driven by an organized cascade of signaling mechanisms. The TGFβ cytokine family and their receptors, which comprise a complex group of multifunctional proteins that are expressed in the mammalian corneal epithelium under normal physiological conditions, but are significantly upregulated following injury, are known regulators of the various events involved during corneal epithelial maintenance and wound healing. Research has shown that a decrease or inhibition of TGFβ signaling has resulted in a delay of corneal wound repair, thus making it an important intrinsic factor in the regulation of cell migration and proliferation during the wound healing process. In the current study, treatment with low molecular weight silk evoked a robust increase in TGFβ2 isoform expression, correlating well with the observed enhancement in cell migration, proliferation, and wound closure. Moreover, treatment with high molecular weight silk resulted in a significant down regulation in the expression of all isoforms of TGFβ, suggesting that the observed decrease in cell migration, proliferation, and scratch wound closure, can be attributed to an inhibitory effect on TGFβ expression and signaling.

The effects of low molecular weight SDP on scratch wound closure was partially attenuated in the presence of a TGFβRI specific inhibitor, which was used to disrupt the TGFβ signaling pathway in HCLE cells during an in vitro scratch assay. Cell migration and wound closure is also attenuated when TGFβ signaling is inhibited during basal conditions, and despite a decrease in SDP's stimulatory effects, the wound closure rate of inhibited cells treated with low molecular weight silk was still faster than control cells treated with the inhibitor alone. This suggests that SDP is at least partially stimulating cell migration and growth through the activation of TGFβ signaling, but is most likely activating multiple signaling pathways that are capable of modulating corneal epithelial cell behavior and increasing cell migration when the TGFβ signaling pathway is inhibited. The ability of SDP to stimulate the expression of genes implicated in corneal wound healing was evaluated, and the effect of fragment size on TGFβ expression was significant. Low molecular weight silk robustly increased TGFβ2 expression while high molecular weight silk had a significant down regulating effect. Furthermore, the use of TGFβRI inhibitor during wound closure revealed that low molecular weight SDP is stimulating an increase in cell growth and migration through TGFβ mediated signaling. The results from the studies described herein further characterize SDP's wound healing effects and reveal the extent of which its bio-functional properties rely on the chemical and molecular attributes of its protein structure. Accordingly, these results demonstrate the use of low molecular weight SDP for improving tissue regeneration and repair of wounds, including ocular wounds, skin wounds and scars.

In exemplary embodiments, the compositions provided herein comprising SDP fragments are derived from *Bombyx mori* silkworm fibroin. (GenBank Accession Nos. P05790).

In some embodiments, the SDP fragments are derived from other exemplary fibroins associated with silk from other insects such as spider and are contemplated for inclusion in the compositions provided herein. Table 1, below, provides an exemplary list of silk-producing species and silk proteins:

TABLE 1

An exemplary list of silk-producing species and silk proteins (adopted from Bini et al. (2003), *J. Mol. Biol.* 335(1): 27-40).

| Accession | Species | Producing gland | Protein |
|---|---|---|---|
| A. Silkworms | | | |
| AAN28165 | *Antheraea mylitta* | Salivary | Fibroin |
| AAC32606 | *Antheraea pernyi* | Salivary | Fibroin |
| AAK83145 | *Antheraea yamamai* | Salivary | Fibroin |
| AAG10393 | *Galleria mellonella* | Salivary | Heavy-chain fibroin (N-terminal) |
| AAG10394 | *Galleria mellonella* | Salivary | Heavy-chain fibroin (C-terminal) |
| P05790 | *Bombyx mori* | Salivary | Fibroin heavy chain precursor, Fib-H, H-fibroin |
| CAA27612 | *Bombyx mandarina* | Salivary | Fibroin |
| Q26427 | *Galleria mellonella* | Salivary | Fibroin light chain precursor, Fib-L. L-fibroin, PG-1 |
| P21828 | *Bombyx mori* | Salivary | Fibroin light chain precursor, Fib-L. L-fibroin |
| B. Spiders | | | |
| P19837 | *Nephila clavipes* | Major ampullate | Spidroin 1, dragline silk fibroin 1 |
| P46804 | *Nephila clavipes* | Major ampullate | Spidroin 2, dragline silk fibroin 2 |
| AAK30609 | *Nephila senegalensis* | Major ampullate | Spidroin 2 |
| AAK30601 | *Gasteracantha mammosa* | Major ampullate | Spidroin 2 |
| AAK30592 | *Argiope aurantia* | Major ampullate | Spidroin 2 |
| AAC47011 | *Araneus diadematus* | Major ampullate | Fibroin-4, ADF-4 |
| AAK30604 | *Latrodectus geometricus* | Major ampullate | Spidroin 2 |
| AAC04503 | *Araneus bicentenarius* | Major ampullate | Spidroin 2 |
| AAK30615 | *Tetragnatha versicolor* | Major ampullate | Spidroin 1 |
| AAN85280 | *Araneus ventricosus* | Major ampullate | Dragline silk protein-1 |
| AAN85281 | *Araneus ventricosus* | Major ampullate | Dragline silk protein-2 |
| AAC14589 | *Nephila clavipes* | Minor ampullate | MiSp1 silk protein |
| AAK30598 | *Dolomedes tenebrosus* | Ampullate | Fibroin 1 |
| AAK30599 | *Dolomedes tenebrosus* | Ampullate | Fibroin 2 |
| AAK30600 | *Euagrus chisoseus* | Combined | Fibroin 1 |
| AAK30610 | *Plectreurys tristis* | Larger ampule-shaped | Fibroin 1 |
| AAK30611 | *Plectreurys tristis* | Larger ampule-shaped | Fibroin 2 |
| AAK30612 | *Plectreurys tristis* | Larger ampule-shaped | Fibroin 3 |
| AAK30613 | *Plectreurys tristis* | Larger ampule-shaped | Fibroin 4 |
| AAK30593 | *Argiope trifasciata* | Flagelliform | Silk protein |
| AAF36091 | *Nephila madagascariensis* | Flagelliform | Fibroin, silk protein (N-terminal) |
| AAF36092 | *Nephila madagascariensis* | Flagelliform | Silk protein (C-terminal) |

TABLE 1-continued

An exemplary list of silk-producing species and silk proteins (adopted from Bini et al. (2003), *J. Mol. Biol.* 335(1): 27-40).

| Accession | Species | Producing gland | Protein |
|---|---|---|---|
| AAC38846 | *Nephila clavipes* | Flagelliform | Fibroin, silk protein (N-terminal) |
| AAC38847 | *Nephila clavipes* | Flagelliform | Silk protein (C-terminal) |

In some examples, the fibroin is isolated from a native source or produced from genetically engineered cells in vivo.

Preparation of SDP Compositions

SDP compositions described herein can possess enhanced stability compared to native fibroin in aqueous solutions. The enhanced stability achieved by the SDP compositions provided herein, which is also referred herein as a SDP, allow the material to remain in solution significantly longer than the native/PASF proteins (referred to herein as PASF). Enhanced stability of the SDP materials provided herein also allow for the preparation of SDP solutions of high concentration without aggregation, precipitation, or gelation. In commercial applications such as eye drops or applications requiring protein to be soluble in solution, enhanced stability can provide suitably lengthy shelf-life and increased quality of the product by reducing protein aggregation. Potential aggregation of protein in solution can negatively impact a product's desired performance for a particular application. The ability to concentrate the SDP to high constitutions in solution (over 50% w/v or >500 mg/mL) is significantly advantageous for inventorying a useful working solution that can be used as-is or diluted for any number of applications. Examples of such applications are the use of SDP fragments as an ingredient in ophthalmic formulations or topical formulation for application to a wound, such as those provided herein, as a protein supplement or additive.

As described herein, transforming the primary amino acid sequences of the native fibroin protein into the SDP material enhanced its stability in aqueous solutions by decreasing the susceptibility of the molecules to aggregate. Aggregation eventually leads to gel formation. In the transformation of the native fibroin, both serine and cysteine amino acids are cleaved in the presence of high heat and dehydrating conditions. Similarly, Patchornik et al. (*J. Am. Chem. Soc.* 1964, 86, 1206) demonstrated that a dehydroalanine (DHA) intermediate is formed from serine and cysteine in solution. The amino acid degradation is further driven when in the presence of a strong dehydrating solvent system, such as the 50-55% w/v LiBr solution as described herein, in which a hydride shift takes place to induce removal of water. The degradation reaction can take place in the presence of hydroxide ions (e.g., pH 7.5 to pH 11), which further drives cleavage of the DHA intermediate. This cleavage forms an amide, a pyruvoyl peptide, and LiBr. One viable chemical mechanism is outlined in Scheme 1 for a serine amino acid, which scheme is also applicable for cysteine amino acids. Chemical alteration of the serine and cysteine amino acids of the PASF protein into a DHA intermediate with further hydrolytic cleavage leads to enhanced solution stability of the SDP products.

Scheme 1. Schematic detailing an underlying chemical reaction for serine and cysteine degradation. Degradation is driven by the production of a DHA intermediate that is formed from a hydride shift reaction in the presence of a dehydrating high salt concentration environment. Degradation of DHA is then accomplished through an $SN_2$ reaction within the basic solvent enviromment.

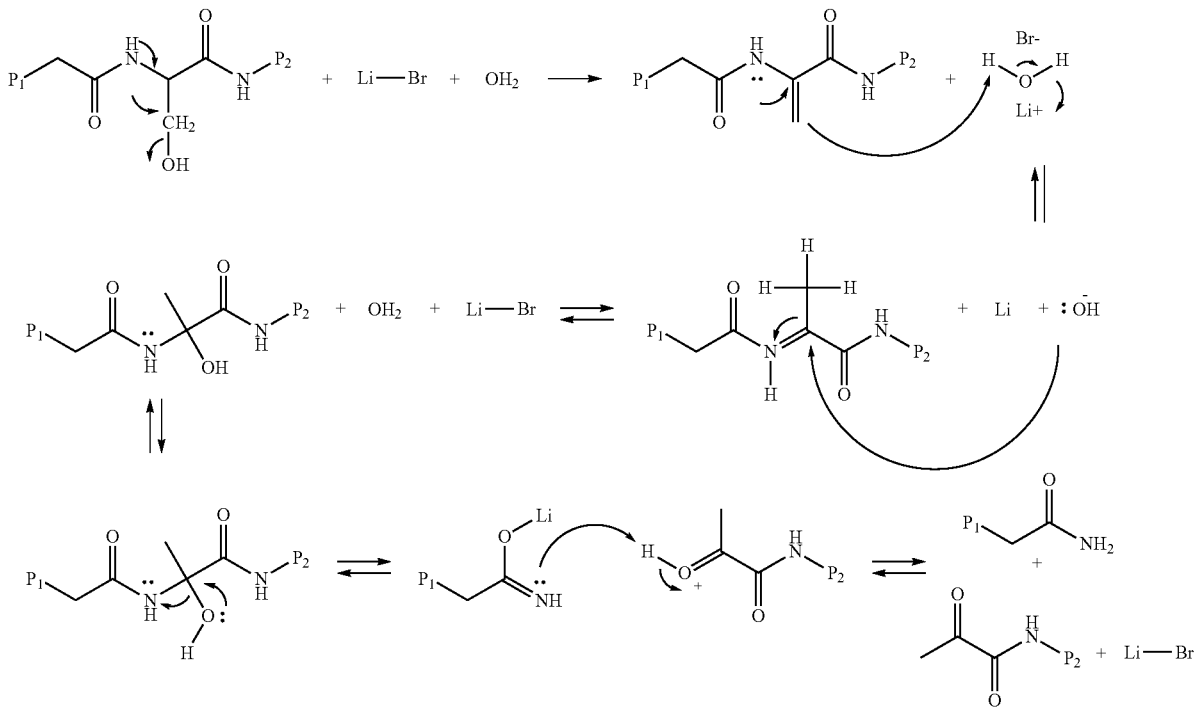

This cleavage reaction discussed above can significantly affect macromolecular properties of the resulting peptides, which results in an aqueous solution of stabilized SDP material. The initial protein aggregation of fibroin is believed to be instigated by interactions of the native fibroin heavy and light chains at the cysteine amino acids as described by Greying et al. (*Biomacromolecules* 2012, 13(3): 676-682). The cysteine amino acids within the fibroin light and heavy protein chains interact with one another through disulfide linkages. These disulfide bridges participate in fibroin protein aggregation and gel network flocculation. Without the native fibroin light chain present, the proteins are significantly less susceptible to aggregation. Therefore, the process described herein can effectively reduce the native fibroin light chain's ability to form disulfide bonds by reducing cysteine content and thus reducing or eliminating disulfide bond-forming capability. Through this mechanism, the transformative process described herein functionally stabilizes the resulting SDP in solution by reducing or eliminating the ability to form cysteine-derived aggregations.

In addition to aggregation-inducing disulfide bridges, the susceptibility of the silk fibroin to further aggregate into flocculated structure is also driven by the protein's amino acid chemistry as described by Mayen et al. (*Biophysical Chemistry* 2015, 197:10-17). Molecular modeling of silk fibroin serine, alanine, and glycine amino acid sequences have shown that the presence of serine enhances initial protein-to-protein interaction through a greater propensity to create hydrogen bonding between adjacent fibroin protein chain moieties. The models demonstrate that reduced serine and increased alanine and glycine decrease the initial propensity for protein aggregation. The molecular modeling observations indicate that by altering the native amino acid chemistry of the fibroin protein a material could be generated that would have higher stability in aqueous solution.

One strategy to accomplish enhanced stability is to eliminate charged functional groups, such as hydroxyls, from the protein. Due to the relatively high electronegativity of hydroxyl groups, this chemistry can drive both hydrogen bonding with available hydrogen atoms and non-specific charge interactions with positively charged amino acid groups. Almost 12% of the native fibroin protein's content is composed of serine, which bears a hydroxyl functional group. Therefore, by reducing the availability of hydroxyl groups that facilitate hydrogen bonding, the overall protein stability in solution s enhanced. The process described herein effectively reduces the amount of serine content and increases the relative alanine and glycine content, which eliminates the number of available hydroxyl groups available to create hydrogen bonds. The process described herein functionally stabilizes the resulting SDP in solution extended periods of time. In some embodiments the SDP in solution is stabilized for at least 3 months, at least 4 months, at least 5 months, at least 6 months, at least 7 months, at least 8 months, at least 9 months, at least 10 months, at least 11 months, at least 1 year, at least 1.5 years, at least 2 years, at least 3 years or longer.

In addition to the reduction of cysteine and serine moieties, solvent charge interaction is important for stabilizing a protein solution. After initial protein flocculation, the gelation process is believed to continue to drive closer associations among the native fibroin heavy chains, which leads to both intra- and inter-molecular beta-sheet formation among hydrophobic blocks of the heavy chains. Once significant beta-sheet formation occurs, the fibroin solution transitions to a gel. As the solution transitions to a gel, and the fibroin becomes insoluble and is no longer useful as a solution-based product. To prevent gelation, the pH of the SDP solution can be raised to high alkalinity to enhance stability, for example over a pH of 7.5. As a result, the increased pH produces additional free hydroxyl groups that form a valence shield around the SDP molecules in solution. The formed valence shield acts to produce a zeta potential that stabilizes the protein by reducing protein-protein interactions derived from hydrogen bonding or non-specific charged and/or hydrophobic interactions. The fibroin-transformation process functionally stabilizes processed SDP in solution through this mechanism and others.

In some embodiments, SDP fragments are prepared by the following process:

1. Silk cocoons are prepared by removing pupae material and pre-rinsing in warm water.

2. Native fibroin protein fibers are extracted from the gum-like sericin proteins by washing the cocoons in water at high water temperature, typically 95° C. or more, at an alkaline pH.

3. The extracted fibroin fibers are dried and then dissolved using a solvent system that neutralizes hydrogen bonding between the beta-sheets; a 54% LiBr aqueous solution of 20% w/v silk fibroin protein is effective for this neutralization step.

4. The dissolved fibroin protein in LiBr solution is processed in an autoclave environment (~121° C. [~250° F.], at ~15-17 PSI pressure, for approximately 30 minutes at temperature).

5. The heat processed fibroin protein and LiBr solution are then dialyzed to remove lithium and bromide ions from solution. At this point in the process the material has been chemically transformed to SDP.

6. The dialyzed SDP is then filtered to remove any non-dissolved aggregates and contaminating bioburden.

The SDP solution is produced using a distinctly different process than the process used for current silk fibroin solution production, as schematically illustrated in FIG. 1. Notably, the autoclaving of the silk fibroin protein while it is combined with LiBr in solution initiates chemical transitions to produce the stabilized SDP material. The fibroin protein is dissolved in LiBr solution, which neutralizes hydrogen bonding and electrostatic interactions of the solubilized native fibroin protein. This leaves the protein without specific secondary structure confirmations in solution. As a result, the thermodynamic energy required to hydrolyze covalent bonding within the fibroin protein chain is at its lowest energy requirements to initiate hydrolytic cleavage.

In one embodiment, the temperature is set to 121° C. for 30 minutes at 15-17 PSI autoclave conditions. However, in various embodiments, the processing conditions are modified to stabilize the SDP material to varying degrees. In other embodiments, additional protein solubilization agents are used in the process, including other or additional halide salts such as calcium chloride and sodium thiocyanate, organic agents such as urea, guanidine hydrochloride, and 1,1,1,3,3,3-hexafluoroisopropanol, additional strong ionic liquid solution additives such as calcium nitrate and 1-butyl-3-methylimidazolium chloride, or a combination thereof.

SDP Compositions

SDP compositions provided herein are derived from silk fibroin and possess enhanced solubility and stability in aqueous solutions. In some embodiments, the SDP compositions provided herein are prepared by a process comprising heating an aqueous fibroin solution at an elevated pressure. The aqueous fibroin solution includes lithium bromide at a concentration of at least 8M. The aqueous fibroin solution is heated to at least about 105° C. (221° F.) under a pressure of at least about 10 PSI for at least about 20 minutes, to provide the protein composition. The polypeptides of the protein composition comprise less than 8.5% serine amino acid residues, and the protein composition has an aqueous viscosity of less than 5 cP as a 10% w/w solution in water.

In some cases, SDP compositions provided herein are prepared by a process comprising heating an aqueous fibroin solution at an elevated pressure, wherein the aqueous fibroin solution comprises lithium bromide at a concentration of 9-10M, and wherein the aqueous fibroin solution is heated to a temperature in the range of about 115° C. (239° F.) to about 125° C. (257° F.), under a pressure of about 15 PSI to about 20 PSI for at least about 20 minutes; to provide the protein composition. The protein composition can include less than 6.5% serine amino acid residues and the protein composition can have an aqueous viscosity of less than 10 cP as a 15% w/w solution in water.

In some embodiments, SDP compositions provided herein can possess enhanced stability in aqueous solution, wherein: the primary amino acid sequences of the SDP composition differs from native fibroin by at least by at least 4% with respect to the combined difference in serine, glycine, and alanine content (SDP vs. PASF); cysteine disulfide bonds between the fibroin heavy and fibroin light protein chains are reduced or eliminated; and the composition has a serine content that is reduced by greater than 25% compared to native fibroin protein. The average molecular weight of the SDP composition can be less than about 100 kDa and greater than about 25 kDa.

In some embodiments, SDP compositions provided herein possess enhanced stability in aqueous solution, wherein: the primary amino acid sequences of the SDP composition differs from native fibroin by at least by at least 6% with respect to the combined difference in serine, glycine, and alanine content; cysteine disulfide bonds between the fibroin heavy and fibroin light protein chains are reduced or eliminated; and the composition has a serine content that is reduced by greater than 40% compared to native fibroin protein. In some embodiments, the average molecular weight of the SDP composition is less than about 96 kDa and greater than about 25 kDa.

In some embodiments, the SDP compositions provided herein possess enhanced stability in aqueous solutions, wherein: the primary amino acid sequences of the SDP composition is modified from native silk fibroin; cysteine disulfide bonds between the fibroin heavy and fibroin light protein chains are reduced or eliminated; the average molecular weight of the SDP composition is less than about 100 kDa and greater than about 25 kDa; and the SDP composition maintains an optical absorbance at 550 nm of less than 0.25 for at least two hours after five seconds of ultrasonication. For example, a 5% w/w solution of the protein composition can maintain an optical absorbance of less than 0.1 at 550 nm after five seconds of ultrasonication at 10 Hz and 20% amplitude, which are the standard conditions used for ultrasonication described herein.

In some embodiments, SDP compositions provided herein possess enhanced stability in aqueous solutions, wherein: the primary amino acid sequences of the SDP composition is modified from native silk fibroin such that they differ from native fibroin by at least by at least 5% with respect to the combined difference in serine, glycine, and alanine content; cysteine disulfide bonds between the fibroin heavy and fibroin light protein chains are reduced or eliminated; the average molecular weight of the SDP composition is less than about 96 kDa and greater than about 25 kDa; and the SDP composition maintains an optical absorbance at 550 nm of less than 0.2 for at least two hours after five seconds of ultrasonication.

In some embodiments, SDP compositions provided herein are isolated and/or purified as a dry powder or film, for example, by dialysis and/or filtration. Alternatively, in some embodiments, SDP compositions provided herein are isolated and/or purified as a stable aqueous solution, In some embodiments, the SDP compositions can be modified for use as a therapeutic formulation, such as an ophthalmic formulation or a topical formulation for application to a skin wound or scar.

In various embodiments, the amino acid compositions of the SDP found in SDP compositions provided herein can differ from the amino acid composition of native fibroin by at least by at least 4%, by at least 4.5%, by at least 5%, or by at least 5.5%, or by at least 6%, with respect to the content of serine, glycine, and alanine combined.

In some embodiments, the SDP compositions provided herein can have a serine content that is reduced by greater than 25%, by greater than 30%, by greater than 35%, by greater than 40%, or by greater than 45%, compared to the serine content of native fibroin protein.

In some embodiments, the average molecular weight of SDP compositions provided herein are less than about 100 kDa, less than about 98 kDa, less than about 96 kDa, less than about 95 kDa, less than about 90 kDa, less than about 85 kDa, less than about 80 kDa, less than about 75 kDa, or less than about 70 kDa. In various embodiments, the average molecular weight of the SDP composition is greater than about 30 kDa, greater than about 35 kDa, greater than about 40 kDa, greater than about 50 kDa, greater than about 60 kDa, or greater than about 70 kDa. Accordingly, in some embodiments, the (weight average) average molecular weight of SDP compositions provided herein is about 30 kDa to about 100 kDa, about 30 kDa to about 96 kDa, about 30 kDa to about 90 kDa, about 35 kDa to about 80 kDa, about 35 kDa to about 70 kDa, about 40 kDa to about 60 kDa. In various embodiments, the average molecular weight of the SDP composition is about 60 kDa to about 80 kDa, about 50 kDa to about 70 kDa, about 40 kDa to about 60 kDa, about 30 kDa to about 50 kDa, about 35 kDa to about 45 kDa, or about 40 kDa to about 43 kDa.

In various embodiments, SDP compositions provided herein can have an aqueous viscosity of less than 4 cP as a 10% w/w solution in water. In some cases, SDP compositions provided herein can have an aqueous viscosity of less than 10 cP as a 24% w/w solution in water.

In some embodiments, SDP compositions provided herein are soluble in water at 40% w/w without any precipitation observable by ocular inspection.

In some cases, certain SDP compositions provided herein do not gel upon ultrasonication of an aqueous solution of the protein composition at concentrations of up to 10% w/w. In some cases, certain SDP compositions provided herein do not gel upon ultrasonication of an aqueous solution of the protein composition at concentrations of up to 15% w/w, up to 20% w/w, up to 25% w/w, up to 30% w/w, up to 35% w/w, or up to 40% w/w.

In some embodiments, SDP compositions provided herein comprise less than 8% serine amino acid residues. In some cases, SDP compositions provided herein comprise less than 7.5% serine amino acid residues, less than 7% serine amino acid residues, less than 6.5% serine amino acid residues, or less than 6% serine amino acid residues.

In some embodiments, SDP compositions provided herein comprise greater than 46.5% glycine amino acids, relative to the total amino acid content of the protein composition. In some cases, SDP compositions provided herein comprise greater than 47% glycine amino acids, greater than 47.5% glycine amino acids, or greater than 48% glycine amino acids.

In some embodiments, SDP compositions provided herein comprise greater than 30% alanine amino acids, relative to the total amino acid content of the protein composition. In some cases, SDP compositions provided herein comprise greater than 30.5% alanine, greater than 31% alanine, or greater than 31.5% alanine.

In some embodiments, SDP compositions provided herein can completely re-dissolve after being dried to a thin film. In various embodiments, SDP compositions provided herein can lack beta-sheet protein structure in aqueous solution. In some cases, SDP compositions provided herein can maintain an optical absorbance in aqueous solution of less than 0.25 at 550 nm after at least five seconds of ultrasonication.

In some embodiments, SDP compositions provided herein are in combination with water. In some cases, SDP compositions provided herein can completely dissolve in water at a concentration of 10% w/w, or even greater concentrations such as 15% w/w, 20% w/w, 25% w/w, 30% w/w, 35% w/w, or 40% w/w. In some embodiments, SDP compositions provided herein are isolated and purified, for example, by dialysis, filtration, or a combination thereof.

In various embodiments, SDP compositions provided herein can enhance the spreading of an aqueous solution comprising the protein composition and ophthalmic formulation components, for example, compared to the spreading of a corresponding composition that does not include the protein composition. This enhanced spreading can result in an increase in surface area of the aqueous solution by greater than twofold, or greater than threefold.

In some embodiments, SDP compositions provided herein do not form a gel at concentrations up to 20% w/v, up to 30% w/v, or up to 40% w/v. In some cases, SDP compositions provided herein can remain in solution up to a viscosity of at least 9.8 cP.

In some embodiments, SDP compositions provided herein have glycine-alanine-glycine-alanine (GAGA) (SEQ ID NO: 9) segments of amino acids that comprise at least about 47.5% of the amino acids of the SDP composition. In some cases, SDP compositions provided herein also have GAGA (SEQ ID NO: 9) segments of amino acids that comprise at least about 48%, at least about 48.5%, at least about 49%, at least about 49.5%, or at least about 50%, of the amino acids of the protein composition.

In various embodiments, SDP compositions provided herein have glycine-alanine (GA) segments of amino acids that comprise at least about 59% of the amino acids of the SDP composition. In some cases, SDP compositions provided herein can also have GA segments of amino acids that comprise at least about 59.5%, at least about 60%, at least about 60.5%, at least about 61%, or at least about 61.5%, of the amino acids of the protein composition.

In some cases, SDP compositions provided herein can have primary amino acid sequences that differ from native fibroin by at least by at least 6% with respect to the combined difference in serine, glycine, and alanine content; an average molecular weight of less than about 100 kDa; and maintain an optical absorbance at 550 nm of less than 0.25 for at least two hours after five seconds of ultrasonication. Thus, for example, a particular SDP composition provided herein can possesses enhanced stability in aqueous solution, wherein: the primary amino acid sequences of the SDP composition differs from native fibroin by at least by at least 6% with respect to the combined difference in serine, glycine, and alanine content; cysteine disulfide bonds between the fibroin heavy and fibroin light protein chains are reduced or eliminated; the composition has a serine content that is reduced by greater than 40% compared to native fibroin protein; and wherein the average molecular weight of the SDP composition is less than about 96 kDa.

In some cases, SDP compositions provided herein can possess enhanced stability in aqueous solutions, wherein: the primary amino acid sequences of the SDP composition is modified from native silk fibroin; cysteine disulfide bonds between the fibroin heavy and fibroin light protein chains are reduced or eliminated; an average molecular weight of less than about 100 kDa; and maintain an optical absorbance at 550 nm of less than 0.25 for at least two hours after five seconds of ultrasonication. In one specific embodiment, the primary amino acid sequences of the SDP composition are modified from native silk fibroin such that they differ from native fibroin by at least by at least 5% with respect to the combined difference in serine, glycine, and alanine content; the average molecular weight of the SDP composition is less than about 96 kDa; and the SDP composition maintains an optical absorbance at 550 nm of less than 0.2 for at least two hours after five seconds of ultrasonication.

Thus, in one specific embodiment, a SDP composition provided herein possess enhanced stability in aqueous solutions, wherein: the primary amino acid sequences of the SDP composition is modified from native silk fibroin such that they differ from native fibroin by at least by at least 5% with respect to the combined difference in serine, glycine, and alanine content; cysteine disulfide bonds between the fibroin heavy and fibroin light protein chains are reduced or eliminated; the average molecular weight of the SDP composition is less than about 96 kDa; and the SDP composition maintains an optical absorbance at 550 nm of less than 0.2 for at least two hours after five seconds of ultrasonication.

In some embodiments, SDP compositions provided herein are prepared by a process comprising heating an aqueous fibroin solution at an elevated pressure, wherein the aqueous fibroin solution comprises lithium bromide at a concentration of at least 8M, and wherein the aqueous fibroin solution is heated to at least about 105° C. (221° F.) under a pressure of at least about 10 PSI for at least about 20 minutes; to provide the protein composition, wherein the protein composition comprises less than 8.5% serine amino acid residues and the protein composition has an aqueous viscosity of less than 5 cP as a 10% w/w solution in water. Therefore, methods of preparing a SDP composition are also provided herein. Methods of preparing a SDP composition provided herein can include one or more of the process steps described herein.

In some cases, methods of preparing provided herein can use lithium bromide having a concentration between about 8.5M and about 11M. In some embodiments, the concentration of lithium bromide is about 9M to about 10M, or about 9.5M to about 10M.

In some embodiments, the aqueous fibroin solution that contains lithium bromide is heated to at least about 107° C. (225° F.), at least about 110° C. (230° F.), at least about 113° C. (235° F.), at least about 115° C. (239° F.), or at least about 120° C. (248° F.).

In some embodiments, the aqueous fibroin solution that contains lithium bromide is heated under a pressure of at least about 12 PSI, at least about 14 PSI, at least about 15 PSI, or at least about 16 PSI, up to about 18 PSI, or up to about 20 PSI.

In some embodiments, the aqueous fibroin solution that contains lithium bromide is heated for at least about 20 minutes, at least about 30 minutes, at least about 45 minutes, or at least about 1 hour, up to several (e.g., 12-24) hours.

In some embodiments, the protein composition has an aqueous viscosity of less than 4 cP as a 10% w/w solution in water. In various embodiments, the protein composition has an aqueous viscosity of less than 10 cP as a 24% w/w solution in water.

In some embodiments, the protein composition are dissolved in water at 40% w/w without observable precipitation.

In some embodiments, the fibroin has been separated from sericin.

In some embodiments, lithium bromide has been removed from the protein composition to provide a purified protein composition. In various embodiments, the protein composition has been isolated and purified, for example, by dialysis, filtration, or a combination thereof.

In various embodiments, the protein composition does not gel upon ultrasonication of an aqueous solution of the composition at concentrations of up to 10% w/w, up to 15% w/w, up to 20% w/w, up to 25% w/w, up to 30% w/w, up to 35% w/w, or up to 40% w/w.

In additional embodiments, the protein composition has properties as described above, and amino acid compositions as described above regarding serine, glycine, and alanine content.

In various embodiments, the protein composition re-dissolves after drying as a thin film. The protein composition can lack beta-sheet protein structure in solution. The protein composition can maintain an optical absorbance in solution of less than 0.25 at 550 nm after at least five seconds of ultrasonication.

In one specific embodiment, the invention provides a protein composition prepared by a process comprising heating an aqueous fibroin solution at an elevated pressure, wherein the aqueous fibroin solution comprises lithium bromide at a concentration of 9-10M, and wherein the aqueous fibroin solution is heated to a temperature in the range of about 115° C. (239° F.) to about 125° C. (257° F.), under a pressure of about 15 PSI to about 20 PSI for at least about 30 minutes; to provide the protein composition, wherein the protein composition comprises less than 6.5% serine amino acid residues and the protein composition has an aqueous viscosity of less than 10 cP as a 15% w/w solution in water.

In some embodiments, SDP compositions are provided that is chemically distinct from native silk fibroin protein. The SDP has enhanced stability in aqueous solution. In some embodiments, the SDP can be used in a method for forming, for example, ophthalmic ingredients with a protein composition described herein, for example, a protein composition aqueous solution. The solution can include about 0.01% to about 92% w/v SDP. In some embodiments, the solution is about 8% to about 99.9% w/v water.

In some embodiments, processes are provided that induces hydrolysis, amino acid degradation, or a combination thereof, of fibroin protein such that the average molecular weight of the protein is reduced from about 100-200 kDa for silk fibroin produced using prior art methods to about 30-90 kDa, or about 30-50 kDa, for the SDP material described herein. In some embodiments, the resulting polypeptides is a random assortment of peptides of various molecular weights averaging to the ranges recited herein. In addition, in some embodiments, the amino acid chemistry is altered by reducing cysteine content to non-detectable levels by standard assay procedures. For example, in some embodiments, the serine content is reduced by over 50% from the levels found in the native fibroin, which can result in increases of overall alanine and glycine content by 5% (relative amino acid content), as determined by standard assay procedures. The process can provide a protein composition where the fibroin light chain protein is not discernable after processing, as well when the sample is run using standard Sodium Dodecyl Sulfate Polyacrylamide Gel Electrophoresis (SDS-PAGE) electrophoresis methods. Furthermore, the resulting SDP material forms minimal to no beta-sheet protein secondary structure post-processing, while silk fibroin solution produced using prior art methods forms significant amounts of beta-sheet secondary structure. In one embodiment, the SDP material is prepared by processing silk fibroin fibers under autoclave or autoclave-like conditions (i.e., approximately 120° C. and 14-18 PSI) in the presence of a 40-60% w/v lithium bromide (LiBr) solution.

In some embodiments, ophthalmic compositions are provided for the treatment of dry eye syndrome in a human or mammal. In some embodiments, the compositions provided herein are an aqueous solution that includes an amount of SDP effective for treating dry eye syndrome. For example, the aqueous solution can include about 0.01% by weight to about 80% by weight SDP. In other embodiments, the aqueous solution includes SDP at about 0.1% by weight to about 10% by weight, or about 0.5% by weight to about 2% by weight. In certain specific embodiments, the ophthalmic composition includes about 0.05% w/v SDP, about 0.1% w/v SDP, about 0.2% w/v SDP, about 0.25% w/v SDP, about 0.5% w/v SDP, about 0.75% w/v SDP, about 1% w/v SDP, about 1.5% w/v SDP, about 2% w/v SDP, about 2.5% w/v SDP, about 5% w/v SDP, about 8% w/v SDP, or about 10% w/v SDP.

In various embodiments, the ophthalmic formulation includes additional components in the aqueous solution, such as a demulcent agent, a buffering agent, and/or a stabilizing agent. In some embodiments, the demulcent agent is hyaluronic acid (HA), hydroxyethyl cellulose, hydroxypropyl methylcellulose, dextran, gelatin, a polyol, carboxymethyl cellulose (CMC), polyethylene glycol, propylene glycol (PG), hypromellose, glycerin, polysorbate 80, polyvinyl alcohol, or povidone. In some embodiments, the demulcent agent is present, for example, at about 0.01% by weight to about 10% by weight, or at about 0.2% by weight to about 2% by weight. In one specific embodiment, the demulcent agent is HA. In various embodiments, the HA is present at about 0.2% by weight of the formulation.

In some embodiments, the buffering or stabilizing agent of an ophthalmic formulation is phosphate buffered saline, borate buffered saline, citrate buffer saline, sodium chloride, calcium chloride, magnesium chloride, potassium chloride, sodium bicarbonate, zinc chloride, hydrochloric acid, sodium hydroxide, edetate disodium, or a combination thereof.

An ophthalmic formulation can further include an effective amount of an antimicrobial preservative. In some embodiments, the antimicrobial preservative is, for example, sodium perborate, polyquarternium-1 (e.g., Polyquad® preservative), benzalkonium (BAK) chloride, sodium chlorite, brimonidine, brimonidine purite, polexitonium, or a combination thereof.

An ophthalmic formulation can also include an effective amount of a vasoconstrictor, an anti-histamine, or a combination thereof. In some embodiments, the vasoconstrictor or antihistamine is naphazoline hydrochloride, ephedrine hydrochloride, phenylephrine hydrochloride, tetrahydrozoline hydrochloride, pheniramine maleate, or a combination thereof.

In one embodiment, an ophthalmic formulation includes an effective amount of SDP fragments as described herein in combination with water and one or more ophthalmic components. In some embodiments, the ophthalmic components are, for example, a) polyvinyl alcohol; b) PEG-400 and hyaluronic acid; c) PEG-400 and propylene glycol, d) CMC and glycerin; e) propylene glycol and glycerin; 0 glycerin, hypromellose, and PEG-400; or a combination of any one or more of the preceding components. In some embodiments, the ophthalmic formulation includes one or more inactive ingredients such as HP-guar, borate, calcium chloride, magnesium chloride, potassium chloride, zinc chloride, and the like. In some embodiments, the ophthalmic formulation includes one or more ophthalmic preservatives such as sodium chlorite (Purite® preservative ($NaClO_2$), polyquad, BAK, EDTA, sorbic acid, benzyl alcohol, and the like. In some embodiments, the ophthalmic components, inactive ingredients, and preservatives are included at about 0.1% to about 5% w/v, such as about 0.25%, 0.3%, 0.4%, 0.5%, 1%, 2%, 2.5%, or 5%, or a range in between any two of the aforementioned values.

Accordingly, SDP compositions are provided herein that possess enhanced stability in aqueous solutions in which the primary amino acid sequence of native fibroin is modified from native silk fibroin, wherein cysteine disulfide bonds between the fibroin heavy and fibroin light protein chains reduced or eliminated; wherein the composition has a serine content that is reduced by greater than 40% compared to native fibroin protein; and wherein the average molecular weight of the silk derived protein is less than about 96 kDa.

Ophthalmic formulations for the treatment of ophthalmic disorders in a human or mammal are provided herein, wherein the ophthalmic formulation comprises water and an effective amount of the SDP as described above. Ophthalmic composition for use as an eye treatment in a human or mammal are provided herein, wherein the ophthalmic composition comprises water, one or more of a buffering agent and stabilizing agent, and an effective amount of the SDP as described above.

The SDP is highly stable in water, where shelf life solution stability is more than twice that of native silk fibroin in solution. For example, the SDP is highly stable in water, where shelf life solution stability is more than 10 times greater compared to native silk fibroin in solution. The SDP material, when in an aqueous solution, does not gel upon sonication of the solution at a 5% (50 mg/mL) concentration. In other embodiments, the SDP material, when in an aqueous solution, does not gel upon sonication of the solution at a 10% (100 mg/mL) concentration.

The SDP material can have the fibroin light chain over 50% removed when compared to native silk fibroin protein. The SDP material can have a serine amino acid content of less than about 8% relative amino acid content, or a serine amino acid content of less than about 6% relative amino acid content.

The SDP material can have a glycine amino acid content above about 46.5%. The SDP material can have an alanine amino acid content above about 30% or above about 30.5%. The SDP material can have no detectable cysteine amino acid content, for example, as determined by HPLC analysis of the hydrolyzed polypeptide of the protein composition.

The SDP material can form 90% less, 95% less, or 98% less beta-sheet secondary protein structures as compared to native silk fibroin protein, for example, as determined by the FTIR analysis described in Example 8 below.

Ophthalmic compositions for use as an eye treatment in a human or mammal are provided herein, the composition comprising an aqueous solution including an effective amount of SDP material as described above, and a buffering or stabilizing agent.

Ophthalmic formulations for the treatment of ophthalmic disorders in human or mammal are provided herein, the formulations comprising an aqueous solution including an effective amount of SDP material with enhanced stability as described herein.

Methods for forming, for example, an ophthalmic composition, with silk protein comprising combining ophthalmic components with the SDP composition are provided herein.

In some embodiments, the SDP compositions provided herein are formulated for topical treatment of a skin wound or a scar. Pharmaceutical topical formulations disclosed herein are formulated in any suitable manner. Any suitable technique, carrier, and/or excipient is contemplated for use with the SDP fragments disclosed herein.

In some embodiments, the SDP compositions provided herein are formulated an aqueous solution, suspension, dispersion, salve, ointment, gel, cream, lotion, spray or paste. In some embodiments, the SDP composition comprises a pharmaceutical carrier, such as, but not limited to phosphate buffered saline, a film, a fiber, a foam, a hydrogel, a matrix, a three-dimensional scaffold, a microparticle, a nanoparticle, a polymer, or a mat. In some embodiments, the protein fragments are attached to a substrate, such as a corneal transplant, a wound dressing, a contact lens, a tissue, a tissue-graft, or a degradable material.

Disclosed herein, in certain embodiments, is a topical formulation of an SDP composition provided herein wherein the topical formulation is administered with (or via) a wound dressing. Wound dressings include, but are not limited to gauzes, transparent film dressings, hydrogels, polyurethane foam dressings, hydrocolloids and alginates. In certain instances, wound dressings promote wound healing. In some instances wound dressings reduce or inhibit aberrant wound healing.

In certain instances, in the treatment of dermal lesions, contacting lesions with a dressing can often disturb injured tissues. The removal of many dressings for wounds such as burns surface lesions that involve a significant area of the skin can cause significant pain and often can re-open at least portions of partially healed wounds. In some instances, the topical formulations described herein are applied as a liquid to the affected area and the liquid gels as a film on the affected area. In some instances the film is a water soluble film and can be removed with water or a mild aqueous detergent, avoiding pain and discomfort associated with the removal of wound dressings. In certain instances, the topical formulation described herein is a dermal film comprising a flexible film made of a polyalkyloxazoline. In some instances, the film has a structural layer made of a polyalkyloxazoline and a pressure sensitive adhesive layer that keeps the film in place.

Disclosed herein, in certain embodiments, is a topical formulation of an SDP composition provided herein wherein the topical formulation is administered via a patch. In some embodiments, a topical SDP formulation disclosed herein is dissolved and/or dispersed in a polymer or an adhesive. In some embodiments, a film, a patch disclosed herein is constructed for continuous, pulsatile, or on demand delivery of an SDP composition provided herein.

In some instances, the topical formulations described herein comprise pressure sensitive adhesives (e.g., polyalkyloxazoline polymers) and allow for application of an adhesive film to an affected area of skin.

In some embodiments, the formulations and compositions disclosed herein are administered as a dermal paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which may be lost and correspondingly increases the amount delivered to the affected area of the skin of an individual. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers.

In certain instances, the formulations are semisolid (e.g., soft solid or thick liquid) formulations that include an SDP composition provided herein dispersed in an oil-in-water emulsion or a water-in-oil emulsion. In certain instances, the compositions are fluid emulsions (e.g., oil-in-water emulsions or a water-in-oil emulsion). In some embodiments, the hydrophobic component of a lotion and/or cream is derived from an animal (e.g., lanolin, cod liver oil, and ambergris), plant (e.g., safflower oil, castor oil, coconut oil, cottonseed oil, menhaden oil, palm kernel oil, palm oil, peanut oil, soybean oil, rapeseed oil, linseed oil, rice bran oil, pine oil, sesame oil, or sunflower seed oil), or petroleum (e.g., mineral oil, or petroleum jelly).

In certain embodiments, the topical formulations described herein comprise SDP compositions that are optionally incorporated within controlled release particles, lipid complexes, liposomes, nanoparticles, microspheres, microparticles, nanocapsules or other agents which enhance or facilitate localized delivery to the skin. An example of a conventional microencapsulation process for pharmaceutical preparations is shown in U.S. Pat. No. 3,737,337, incorporated herein by reference for such disclosure.

In some instances, a topical formulation described herein is a liposomal formulation. Liposomes are prepared by introducing an aqueous buffer into a mixture of phospholipid and organic solvent and the organic solvent is subsequently removed by evaporation under reduced pressure. An example of a liposomal preparation is described in Proc. Natl. Acad. Sci. 1978, 75, 4194-98, incorporated herein by reference for such disclosure. Liposomes are fractionated according to their particle sizes by size exclusion chromatography (SEC). The subfractions of liposomes are further sized by photon correlation spectroscopy (PCS) for their particle sizes. Enzymatic assays (e.g., phosphatidylcholine (PC) assay) are used to analyze lipid contents of liposomes.

Disclosed herein, in certain embodiments, is a topical formulation of an SDP composition provided herein wherein the topical formulation comprises a carrier. Suitable carriers include water, hyaluronan, collagen, ethanol, polyols (propyleneglycol, polyethylene-glycol, glycerol, cremophor and the like), vegetable oils (such as olive oil), injectable organic esters (e.g., ethyl oleate), fatty oils (e.g., sesame oil), and synthetic fatty acid esters (e.g., ethyl oleate or triglycerides).

Disclosed herein, in certain embodiments, is a topical formulation of an SDP composition provided herein wherein the topical formulation comprises a penetration enhancer. Penetration enhancers include, but are not limited to, sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween 80, nonylphenoxypolyethylene (NP-POE), polysorbates, sodium glycocholate, sodium deoxycholate, sodium taurocholate, sodium taurodihydrofusidate, sodium glycodihydrofusidate, oleic acid, caprylic acid, mono- and di-glycerides, lauric acids, acylcholines, caprylic acids, acylcarnitines, sodium caprates, EDTA, citric acid, salicylates, DMSO, decylmethyl sulfoxide, ethanol, isopropanol, propylene glycol, polyethylene glycol, glycerol, propanediol, and diethylene glycol monoethyl ether. In certain embodiments, the topical formulations described herein are designed for minimal systemic exposure and include, for example, low amounts of penetration enhancers.

Disclosed herein, in certain embodiments, is a topical formulation of an SDP composition provided herein wherein the topical formulation comprises a gelling (or thickening) agent. In some embodiments, a topical formulation disclosed herein further comprises from about 0.1% to about 5%, from about 0.1% to about 3%, or from about 0.25% to about 2%, of a gelling agent. In certain embodiments, the viscosity of a topical formulation disclosed herein is in the range from about 100 to about 500,000 cP, about 100 cP to about 1,000 cP, about 500 cP to about 1500 cP, about 1000 cP to about 3000 cP, about 2000 cP to about 8,000 cP, about 4,000 cP to about 10,000 cP, about 10,000 cP to about 50,000 cP. Suitable gelling agents for use in preparation of the gel topical formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, acacia (gum arabic), agar, aluminum magnesium silicate, sodium alginate, sodium stearate, bladderwrack, bentonite, carbomer, carrageenan, carbopol, xanthan, cellulose, microcrystalline cellulose (MCC), ceratonia, chondrus, dextrose, furcellaran, gelatin, ghatti gum, guar gum, hectorite, lactose, sucrose, maltodextrin, mannitol, sorbitol, honey, maize starch, wheat starch, rice starch, potato starch, gelatin, sterculia gum, polyethylene glycol (e.g. PEG 200-4500), gum tragacanth, ethyl cellulose, ethyl hydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), or combinations thereof.

Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates).

Suitable agents for use in formulations that are applied as liquids and gel upon application to the skin into a film include but are not limited to polymers composed of polyoxypropylene and polyoxyethylene that are known to form thermoreversible gels when incorporated into aqueous solutions. These polymers have the ability to change from the liquid state to the gel state at temperatures close to body temperature, therefore allowing useful formulations that are applied as gels and/or films to the affected area. Examples of polymers that gel at body temperature and are used in gels and/or films described herein include and are not limited to poloxamers (e.g., PLURONICS F68®, F88®, F108®, and F127®, which are block copolymers of ethylene oxide and propylene oxide). The liquid state-to-gel state phase transition is dependent on the polymer concentration and the ingredients in the solution.

Disclosed herein, in certain embodiments, is a topical formulation of an SDP composition provided herein wherein the topical formulation comprises an emollient. Emollients include, but are not limited to, castor oil esters, cocoa butter esters, safflower oil esters, cottonseed oil esters, corn oil esters, olive oil esters, cod liver oil esters, almond oil esters, avocado oil esters, palm oil esters, sesame oil esters, squalene esters, kikui oil esters, soybean oil esters, acetylated monoglycerides, ethoxylated glyceryl monostearate, hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate, oleyl myristate, oleyl stearate, and oleyl oleate, pelargonic acid, lauric acid, myristic acid, palmitic acid, stearic acid, isostearic acid, hydroxystearic acid, oleic acid, linoleic acid, ricinoleic acid, arachidic acid, behenic acid, erucic acid, lauryl alcohol, myristyl alcohol, cetyl alcohol, hexadecyl alcohol, stearyl alcohol, isostearyl alcohol, hydroxystearyl alcohol, oleyl alcohol, ricinoleyl alcohol, behenyl alcohol, erucyl alcohol, 2-octyl dodecanyl alcohol, lanolin and lanolin derivatives, beeswax, spermaceti, myristyl myristate, stearyl stearate, carnauba wax, candelilla wax, lecithin, and cholesterol.

In certain embodiments, a topical formulation comprising an SDP composition provided herein comprises additional excipients such as, by way of example, abrasives, absorbents, anticaking agents, astringents, essential oils, fragrances, skin-conditioning agents, skin healing agents, skin protectants (e.g., sunscreens, or ultraviolet light absorbers or scattering agents), skin soothing agents, or combinations thereof.

The following Examples are intended to illustrate the above inventions and should not be construed as to narrow its scope. One skilled in the art will readily recognize that the Examples suggest many other ways in which the inventions could be practiced. It should be understood that numerous variations and modifications can be made while remaining within the scope of the inventions.

Example 1: SDP Preparation and the Lawrence Stability Test

Materials.

Silkworm cocoons were obtained from Tajima Shoji Co., Ltd., Japan. Lithium bromide (LiBr) was obtained from FMC Lithium, Inc., NC. An autoclave was obtained from Tuttnauer Ltd., NY. The 3,500 Da molecular-weight cutoff (MWCO) dialysis membranes were obtained from Thermo-Scientific, Inc., MA. An Oakton Bromide ($Br^-$) double-junction ion-selective electrode was obtained from ISE, Oakton Instruments, IL.

Processing.

Two samples, SDP and PASF, were prepared as illustrated in FIG. 1. Briefly, SDP was produced by submerging pupae-free, cut silkworm cocoons (3-5 cuts/cocoon) into 95° C. heated, deionized water ($diH_2O$) containing 0.3 wt % $NaCO_3$ at 233 mL water/gram of cocoons. Cocoons were agitated in this solution for 75 minutes to dissolve sericin, thereby separating it from the silk fibers. The cocoons were subsequently washed four times in like dilutions of $diH_2O$ for 20 minutes per rinse to remove residual sericin from the washed silk fibers. The fibers were then dried in a convection oven at 60° C. for 2 hours, weighed, and dissolved in 54 wt % LiBr in water at a ratio of 4× LiBr volume per gram of extracted fiber. This solution was covered and then warmed in a convection oven at 60° C. for 2 hours to expedite extracted fiber dissolution. The solution was then placed in an autoclave and exposed to sterilization conditions (121° C., 17 PSI, 90-100% humidity) for 30 minutes to facilitate fibroin transformation. The resulting solution was allowed to cool to room temperature, then diluted to 5% fibroin with $diH_2O$ and dialyzed to remove LiBr salts using a 3,500 Da MWCO membrane. Multiple exchanges were performed in $diH_2O$ until $Br^-$ ions were less than 1-ppm as determined in the hydrolyzed fibroin solution read on an Oakton Bromide ($Br^-$) double-junction ion-selective electrode. The solution was then further filtered using a 1-5 µm porosity filter followed by filtration through a 0.2 µm polishing filter. This product is referred to as 'SDP Solution' in FIG. 2.

Figure 2:
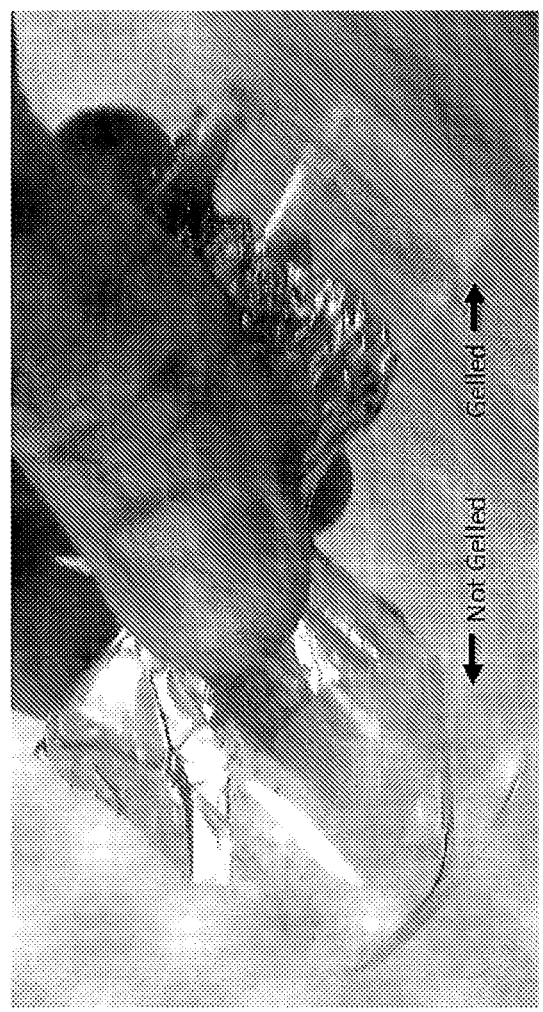
FIG. 2 shows a picture showing results of the Lawrence Stability Test for a stable SDP solution (Sample 1, on left, produced by the process described in Example 1), and a PASF solution (Sample 2, on right, produced by standard hydrolysis conditions). Visual inspection reveals that Sample 1 is a stable aqueous solution that has not gelled, while Sample 2 has gelled, and therefore is not a stable aqueous solution.

A 'control' silk fibroin solution was prepared as illustrated in FIG. 1 to provide the 'PASF Solution' shown in FIG. 2. Except the autoclave step, the same process was performed as described above. A sampling volume (5 mL) from each sample was placed in separate 20 mL glass beakers and the beakers were sealed with foil. The samples were then subjected to the Lawrence Stability Test.

The Lawrence Stability Test is performed by placing the aqueous protein test solution (5% w/v, 50 mg/mL) within the autoclave chamber. The autoclave is then activated for a cycle at 121° C., 17 PSI, for 30 minutes, at 97-100% humidity. After completion of the cycle, the solution is allowed to cool and is then removed from the autoclave chamber. The solution is then shaken to observe solution gelation behavior. If the solution has gelled upon shaking for ~10 seconds, the sample fails the Lawrence Stability Test. Failing the test indicates that the material is inherently unstable as a protein solution.

The Lawrence Stability Test was performed on both the SDP Solution and the PASF Solution. The PASF Solution sample gelled immediately and therefore failed the Lawrence Stability Test. Conversely, the SDP Solution sample remained in solution indefinitely and therefore passed the Lawrence Stability Test. The lack of gelation can be attributed to the fact that SDP Solution production incorporated the autoclave-processing step as indicated in FIG. 1 above. An image of the different test results (not-gelled vs. gelled) is shown in FIG. 2.

Example 2: SDP Molecular Weight Characterization

To evaluate the effect of processing on the molecular weight distribution of solubilized protein, SDP Solution and PASF Solution were subjected to polyacrylamide gel electrophoresis (PAGE), which separates proteins by molecular weight. Specifically, 15 μg of each sample was mixed with running buffer containing sodium dodecyl sulfate and dithiothreitol (Biorad Inc., CA) to remove any secondary folding structures and disulfide bonds, respectively. The mixtures were then heated to 70° C. for 5 minutes. The mixtures were loaded along with a 2.5-200 kDa molecular weight ladder (Life Technologies, CA) onto pre-cast, 4-12% polyacrylamide gradient gels containing Bis-Tris buffer salts (Life Technologies, CA), and then exposed to 120V electric field for 90 minutes on a BioRad PowerPac Power supply (BioRad Inc., CA). The gels were then removed and placed in Coomassie Blue stain for 12 hours to stain proteins, followed by 6 hours of washing in diH$_2$O. The gels were then scanned on a Biorad GS-800 Calibrated Desitometer (BioRad Inc., CA).

Figure 3:
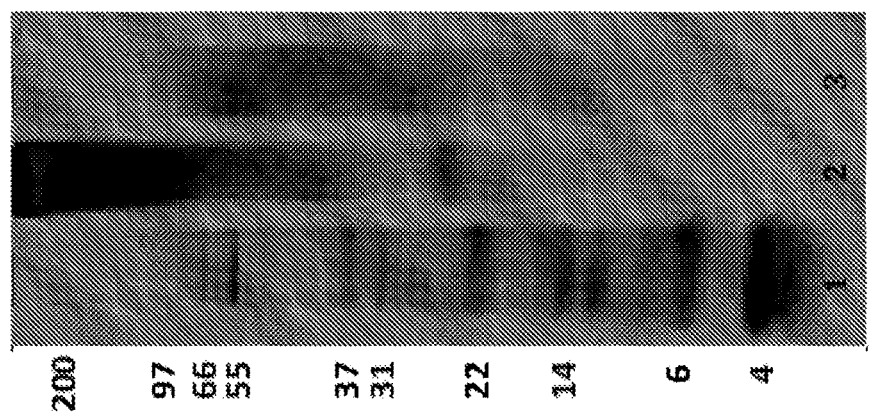
FIG. 3 shows a picture of a gel showing process-mediated modification of aqueous silk fibroin protein to SDP solution. The picture shows the molecular weight (MW) distribution of an SDP Solution (Lane 3, autoclaved) versus a PASF solution (Lane 2, non-autoclaved). A protein standard ladder (Lane 1) and associated weights (numbers to the left of Lane 1) are provided as a reference of MW. A prominent MW band at 23-26 kDa in Lane 2 is noteworthy and is entirely absent following the autoclaving process, indicating that degradation of the fibroin light chain contributes to the enhanced stability of the SDP protein material. Also a clear shift is observed in MW range of fibroin protein following autoclaving (Lane 3), indicating modification of the natural silk fibroin protein to the SDP material composition.

The resulting gel is shown in FIG. 3. The results show that the processing employed to prepare the SDP solution significantly shifts the average molecular weight from 150-200 kDa to less than 80 kDa (FIG. 3). The shift in molecular weight clearly indicates a transformation of the primary and/or secondary structure of the original native fibroin. In addition, the fibroin light chain of fibroin is not present in the SDP after the autoclaving process (visible at 23-26 kDa in Lane 2 for the prior art fibroin), which indicates that the fibroin light chain portion of the protein has been degraded or removed by the processing. These results demonstrate that the autoclave processing transforms the native fibroin protein to a new material that has smaller peptide fragments than the native fibroin protein. The process further degrades/modifies the fibroin light chain. These transformations result in an SDP material that possesses enhanced solution stability as a result of these chemical changes.

Example 3: SDP Stability Study

To further determine the functional impact of the autoclave process on the stability of the resulting SDP compared to the stability of prior art fibroin, the samples were analyzed using the methods of Wang et al. (*Biomaterials* 2008, 29(8):1054-1064) to mimic a well-characterized model of silk fibroin protein gelation. Volumes of both samples (0.5 mL, SDP and PASF) were added to 1.7 mL clear centrifuge tubes and were subjected to ultrasonication (20% amplitude, 10 Hz, 15 seconds). The clear tubes containing the solutions were then visually monitored for gel formation as a screen for gelation.

Figure 4:
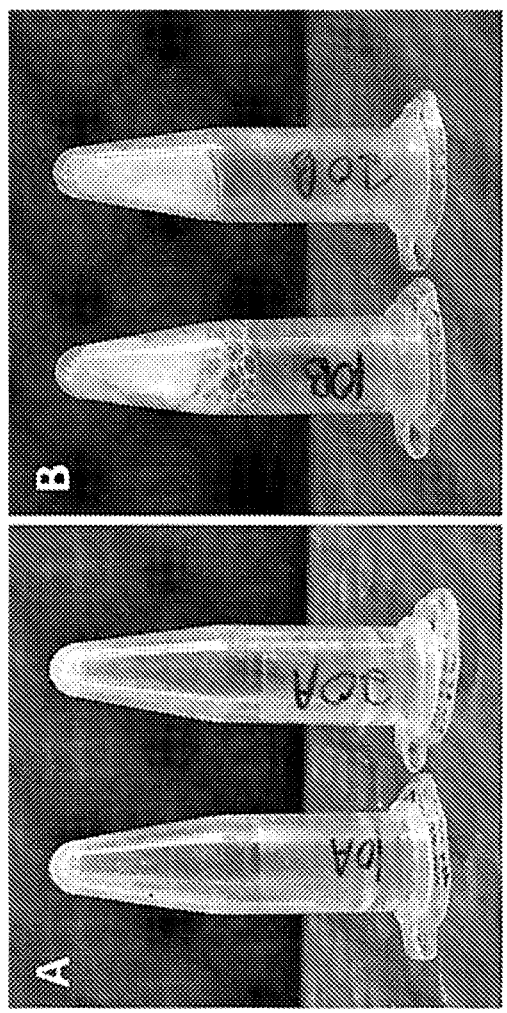
FIG. 4A-B show images demonstrating that (A) SDP Solution material does not gel, while (B) PASF solution material gelled within 2 hours following ultrasonication.

The SDP Solution samples failed to form gels, as shown in FIG. 4A. Even 3 months post-sonication, the SDP samples remained in solution and lacked protein aggregation as determined by visual inspection. The PASF Solution sample gelled rapidly (within 2 hours) following sonication. The resulting gelled PASF is shown in FIG. 4B. These results further indicate that the autoclave process transforms the prior art fibroin to a new material and induces stability to the resulting SDP material.

Example 4: Wound Treatment

Severe traumatic corneal injuries can render the naturally occurring wound healing process insufficient to restore a healthy corneal epithelium, resulting in permanent vision impairment. SDP has been shown to significantly enhance corneal wound healing; however, little work has been done to understand the mechanistic foundations of SDP's beneficial effects and to characterize the proteins chemical and molecular attributes responsible for its wound healing properties. As described in the present application, high and low molecular weight SDP fragments were isolated from the SDP composition described above to evaluate and characterize the influence of protein fragment size on SDP's ability to modulate corneal epithelial cell behaviors that might be involved in the wound healing process.

When added to cell culture, low molecular weight SDP fragments were found to significantly increase cell migration, proliferation, and accelerate in vitro scratch wound closure rate. In some embodiments, the SDP fragments of low molecular weight have a molecular weight of less than about 100 kDa, less than about 90 kDa, less than about 80 kDa, less than about 70 kDa, less than about 60 kDa, less than about 50 kDa, less than about 40 kDa, less than about 30 kDa, less than about 20 kDa, or less than about 10 kDa. In some embodiments, the protein fragment composition isolated from the regenerated SDP composition has an average molecular weight between about 30 kDa and 60 kDa. In some embodiments, at least 75 percent of the SDP fragments in the protein fragment composition have a molecular weight of less than about 100 kDa. In some embodiments, at least 90 percent of the SDP fragments in the protein fragment composition have a molecular weight of less than about 100 kDa. In some embodiments, at least 75 percent of the SDP fragments in the protein fragment composition have a molecular weight of less than about 80 kDa. In some embodiments, at least 90 percent of the SDP fragments in the protein fragment composition have a molecular weight of less than about 80 kDa. In some embodiments, at least 75 percent of the SDP fragments in the protein fragment composition have a molecular weight of less than about 60 kDa. In some embodiments, at least 90 percent of the SDP fragments in the protein fragment composition have a molecular weight of less than about 60 kDa to promote cell migration and proliferation in the tissue to close the wound. In some embodiments, at least 75 percent of the SDP fragments in the protein fragment composition have a molecular weight of less than about 50 kDa. In some embodiments, at least 90 percent of the SDP fragments in the protein fragment composition have a molecular weight of less than about 50 kDa. In some embodiments, at least 75 percent of the SDP fragments in the protein fragment composition have a molecular weight between about 30 kDa and 60 kDa. In some embodiments, at least 90 percent of the SDP fragments in the protein fragment composition have a molecular weight between about 30 kDa and 60 kDa. In some embodiments, at least 75 percent of the SDP fragments in the protein fragment composition have a molecular weight of less than about 30 kDa. In some embodiments, at least 90 percent of the SDP fragments in the protein fragment composition have a molecular weight of less than about 30 kDa. In some embodiments, at least 75 percent of the SDP fragments in the protein fragment composition have a molecular weight of between about 10 kDa and 30 kDa. In some embodiments, at least 90 percent of the SDP fragments in the protein fragment composition have a molecular weight of between about 10 kDa and 30 kDa. In some embodiments, at least 75 percent of the SDP fragments in the protein fragment composition have a molecular weight of less than about 10 kDa. In some embodiments, at least 90 percent of the SDP fragments in the protein composition have a molecular weight of less than about 10 kDa. In some embodiments, at least 50 percent of the SDP fragments in the protein composition have a molecular weight of greater than about 60 kDa.

By contrast, high molecular weight silk did not have any effects on cell proliferation and viability, but was found to significantly decrease cell migration and wound closure, and significantly increase cell-substrate adhesion or cell adhesion to its basement membrane or basement membrane formation. In some embodiments, the SDP fragments of high molecular weight have a molecular weight greater than about 30 kDa, greater than about 40 kDa, greater than about 50 kDa, 60 kDa, greater than about 70 kDa, greater than about 80 kDa, greater than about 90 kDa, or greater than about 100 kDa. In some embodiments, at least 50 percent of the SDP fragments in the protein fragment composition have a molecular weight of greater than about 60 kDa.

Low molecular weight SDP fragments affect the rate at which a wound heals or closes. High molecular weight SDP fragments appear affect how the wound heals or closes (e.g. wound profile). In some embodiments, a protein fragment composition containing both low molecular weight SDP fragments and high molecular weight SDP fragments is used to treat a wound. In some embodiments, a protein fragment composition contains about 50% SDP fragments that have molecular weight less than about 60 kDa and about 50% SDP fragments having molecular weight greater than about 60 kDa.

In some situations, it is desirable to heal a wound fast rather than to heal a wound correctly, for example, healthy person desiring to reduce pain after surgery (e.g. post refractive surgery), injured military persons, persons in areas where infection is rampant, etc. In some embodiments, in these situations, a protein fragment composition contains more of the low molecular weight SDP fragments than it contains high molecular weight SDP fragments. For example, in some embodiments, the protein fragment composition contains about 75% SDP fragments that have molecular weights less than 60 kDa and about 25% SDP fragments that have molecular weights more than 60 kDa.

In some embodiments, the type of wounds also dictate whether high molecular weight SDP fragments or low molecular weight SDP fragments are used to treat the wound. Low molecular weight SDP fragments have anti-inflammatory properties, and wounds that fester can treated with low molecular weight SDP fragments. Some wounds require focus on cell adhesion to the basement membrane or basement membrane formation. Some examples of such wounds include skin burns and diabetic ulcers. In these situations, in some embodiments, a protein fragment composition contains more of the high molecular weight SDP fragments than it contains low molecular weight SDP fragments. For example, in some embodiments, the protein fragment composition contains about 75% SDP fragments that have molecular weights greater than 60 kDa and about 25% SDP fragments that have molecular weights less than 60 kDa.

While not bound by any theory, such actions are likely through clustering of focal adhesions and re-organization of the actin cytoskeleton. Moreover, low molecular weight silk was found to upregulate TGFβ2 expression, while the expression of all TGFβ isoforms was significantly down regulated with high molecular weight silk. In addition, the effects of low molecular weight SDP on scratch wound closure was partially attenuated in the presence of TGFβRI specific inhibitor, suggesting that TGFβ mediated signaling partially contributes to SDP's stimulatory effects on human corneal limbal-epithelial (HCLE) cell migration and proliferation. These findings demonstrate the extent to which SDP's bio-functional and wound healing properties rely on the chemical and molecular attributes of its protein structure.

Silk fibroin protein, derived from *Bombyx mori* silkworm cocoons, has been selected for tissue engineering and regenerative medicine applications due to its desirable set of controllable material features and its ability to be processed into a variety of biomaterial formats. Prior studies have reported that silk fibroin based materials exhibit high biocompatibility, controlled degradability, and inherent non-immunogenic and non-inflammatory properties when used in vivo, thus providing a number of advantages over other bio-polymers for use in a wide range of biomedical applications. Moreover, our previous research efforts have shown that regenerated silk fibroin protein solution stimulates in vitro corneal epithelial cell growth, migration, adhesion, and promotes tissue regeneration leading to an enhanced corneal wound healing response when applied therapeutically on the ocular surface in an in vivo rabbit corneal wound healing model, demonstrating its use for ocular surface repair applications.

Although regenerated silk fibroin has been successfully used as a therapeutic agent to enhance tissue regeneration, there is a need to understand its bio-functional properties at the molecular level in order to provide improved methods of using silk fibroin. Research efforts have demonstrated that the versatility of silk as a biomaterial arises from the fibroin protein's chemical and molecular attributes, which can be heavily influenced by the processing methods used to prepare regenerated silk fibroin solution from raw silk worm cocoons. Exposure of the silk fibroin protein to harsh denaturing conditions affects the intrinsic molecular structure of the protein and leads to differences in molecular weight distribution of the regenerated silk fibroin solution. While studies have reported the effects of silk fibroin molecular weight distribution on its mechanical properties, biocompatibility, proteolytic degradability, and thermal stability, the effects of molecular weight distribution on silk fibroin's wound healing properties have not been investigated in detail.

In the Examples provided herein, the influence of molecular weight distribution on SDP's ability to modulate corneal epithelial cell behaviors involved in the wound healing process was evaluated and characterized. Centrifugal filters were used to fractionate regenerated SDP solution into high and low molecular weight SDP fragments in order to investigate the influence of silk protein fragment size on epithelial cell behavior. Time-lapse imaging was used to track the migration of HCLE cells cultured in the presence of different molecular weight size silk fragments. The effects of SDP protein molecular weight on epithelial cell proliferation were evaluated using MTT colorimetric viability assay.

Additionally, the effect of protein fragment size on the ability of SDP to stimulate epithelial cell-substrate adhesion was assessed using a parallel plate flow chamber system and immunofluorescence staining of focal adhesion protein vinculin. An in vitro scratch assay was then used to model a corneal abrasion, where confluent HCLE cell sheets were partially denuded and subsequently treated with SDP fragments of different molecular weight to evaluate the influence on SDP's wound healing properties during scratch closure. The influence of fibroin molecular weight on the genetic expression of cytokine transforming growth factor beta (TGFβ), which has been implicated to play a critical role in the corneal epithelial wound healing process, was evaluated using quantitative PCR. Finally, HCLE cells were treated with a TGFβ-RI specific inhibitor to disrupt the TGFβ signaling pathway in order to elucidate the molecular pathways which underlie SDP's wound healing effects.

Results from the study suggest a well-defined relationship between SDP molecular weight and its influences on the behavior and performance of SDP based materials. For example, the inventors have demonstrate a link between SDP fragment size and differences in its wound healing properties. Accordingly, methods of using of SDP according to its fragment size as a biomaterial for ocular surface regeneration are provided.

Figure 5:
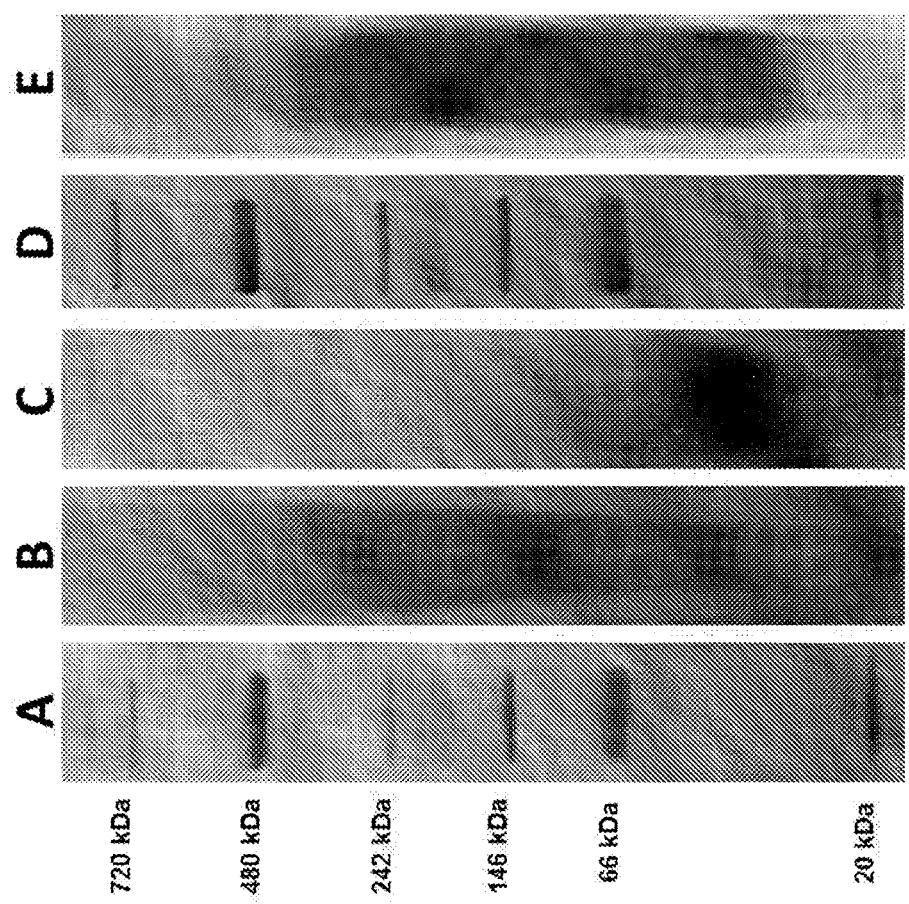
FIG. 5 illustrates Sodium Dodecyl Sulfate Polyacrylamide Gel Electrophoresis (SDS-PAGE) analysis of regenerated SDP solutions of various molecular weight range distributions. An aqueous SDP solution was fractionated into (B) high molecular weight and (C) low molecular weight SDP fragments, and their molecular weight distributions were compared to the (E) unfractionated SDP solution. (A, D) Molecular weight protein marker.

Example 5: Fractionation and Molecular Weight Distribution of SDP Protein Solutions Fractionation of the regenerated SDP solution was accomplished through a series of centrifugation steps utilizing Amicon Ultra 15 mL centrifugal filters of 100, 50, 30, and 10 kDa MW cutoffs (EMD-Millipore, MA, USA). In order to evaluate the molecular weight range of the fractionated SDP solutions, the electrophoretic mobility of the SDP protein was visualized using SDS-PAGE and compared to that of unfractionated SDP solution (FIG. 5). SDS-PAGE of the unfractionated SDP indicated a wide molecular weight distribution of SDP protein within the solution, as evidenced by a large smear located approximately between the 300 kDa and 30 kDa molecular mass ranges. Fractionation of the regenerated SDP solution, however, produced solutions of high and low molecular weight SDP protein. When compared to unfractionated SDP solution, SDS-PAGE of the high molecular weight solution produced a smear indicating an approximate molecular weight distribution between the 300 kDa and 100 kDa range, while the low molecular weight solution produced a smear indicating a molecular weight distribution predominantly in the 30 kDa range, and thus confirming the fractionation of SDP into high and low molecular weight SDP protein solutions.

Example 6: SDP Solution Fractionation

A 50 mg/mL aqueous SDP solution derived from *Bombyx mori* silkworm cocoons was kindly provided by Silk Technologies, Inc. (Plymouth, Minn.), and utilized for all the described studies below. Fractionation of SDP fragments was accomplished using Amicon Ultra 15 mL centrifugal filters of 100, 50, 30, and 10 kDa MW cutoffs (EMD-Millipore, MA, USA). Briefly, 15 mL of a 40 mg/mL SDP stock solution was added to a centrifugal filter with 100 kDa MW cutoff and spun down at 4,000×g for 30 minutes for isolation of SDP fragments of 100 kDa MW and above. The isolated concentrate was collected and the filtrate was subsequently transferred to a centrifugal filter with 50 kDa MW cutoff and spun down again at 4,000×g for 30 minutes to isolate SDP fragments of ~50 kDa MW. The isolated concentrate was collected and the filtrate was then transferred to a centrifugal filter with 30 kDa MW cutoff and spun down again at 4,000×g for 30 minutes to isolate SDP fragments of ~30 kDa MW. The isolated concentrate was collected and the filtrate was then transferred to a centrifugal filter with 10 kDa MW cutoff and spun down again at 4,000×g for 30 minutes to isolate SDP fragments of ~10 kDa MW. The collected concentrates from each MW cutoff were individually washed, 6 times, with 5 mL of $dH_2O$ and spun down again at 4,000×g for 30 minutes using centrifugal filters with the respective MW cutoff filter size for each concentrate. Fractionation of SDP fragments was verified using SDS-PAGE and Coomassie blue R-250 staining (Gibco, Invitrogen Corporation, Grand Island, N.Y., USA).

The effect of SDP protein molecular weight distribution on modulating epithelial cell behavior was first investigated using an in vitro epithelial cell migration assay. HCLE cells were chosen as a reliable cell model for in vitro studies, based on the cell line's highly characterized history and reliability when working with new biomaterials such as SDP. Our previous research efforts have successfully demonstrated an increase in epithelial cell migration and proliferation, and an acceleration in scratch wound closure in vitro, when cells were treated with 4 mg/mL of unfractionated SDP solution, and thus it was used as a positive control for SDP's stimulatory effects throughout the current study.

Example 7: Scratch Wound Closure Assay

A scratch-wound assay with HCLE cells was used to determine the effect of SDP protein fragment size on wound closure in vitro. HCLE cells were seeded within 24 well plates (VWR Radnor, Pa., USA), at $5 \times 10^4$ cells/$cm^2$, and allowed to incubate for a 24 hour period in K-SFM media to form a confluent monolayer of cells. The K-SFM media was removed and the confluent sheet of cells was wounded by scratching with a 100 μl pipette tip, creating a cell free denuded area. The scratch-wounded HCLE cells were washed with 1×PBS to remove any cell fragments or detached cells before incubating in fresh K-SFM media containing increasing concentrations (1 mg/mL, 2 mg/mL, and 4 mg/mL) of high molecular weight or low molecular weight SDP protein solution for 20 hours. Cells were treated with fresh K-SFM media containing 4 mg/mL of unfractionated SDP protein solution or PBS vehicle as a positive control and negative control, respectively. Cell migration was monitored using the microscope's 24-well plate micro-incubator (PeCon, GmbH; M24 S1). A Zeiss Observer Z1 microscope (Carl Zeiss, AG) with 10× objective, 1.6× Opto Var., and phase contrast filter was used to sequentially analyze the wound closure during the course of the assay. The microscope's Mark-and-Find feature was used to memorize select positions within each well to capture multiple areas along the denuded surface. Time-lapse phase contrast imaging was utilized to record a frame every 15-minutes over the 20 hour incubation period with an AxioCam single-channel camera and AxioVision software (Carl Zeiss, AG).

To ensure that wounds with the same wound areas were compared, the area of the wound was traced and measured using ImageJ software, for the multiple positions within each well. Time-lapse images for each position in the wells were analyzed and the wound areas were measured to determine the percentage of wound closure at several time points throughout the course of the assay. The time points at which the wounds fully healed were recorded. The wound closure by HCLE cells in response to treatment with high molecular weight or low molecular weight SDP fragments, was compared to that of cells treated with unfractionated SDP solution, as well as PBS vehicle control.

Figures 8A, 8B:
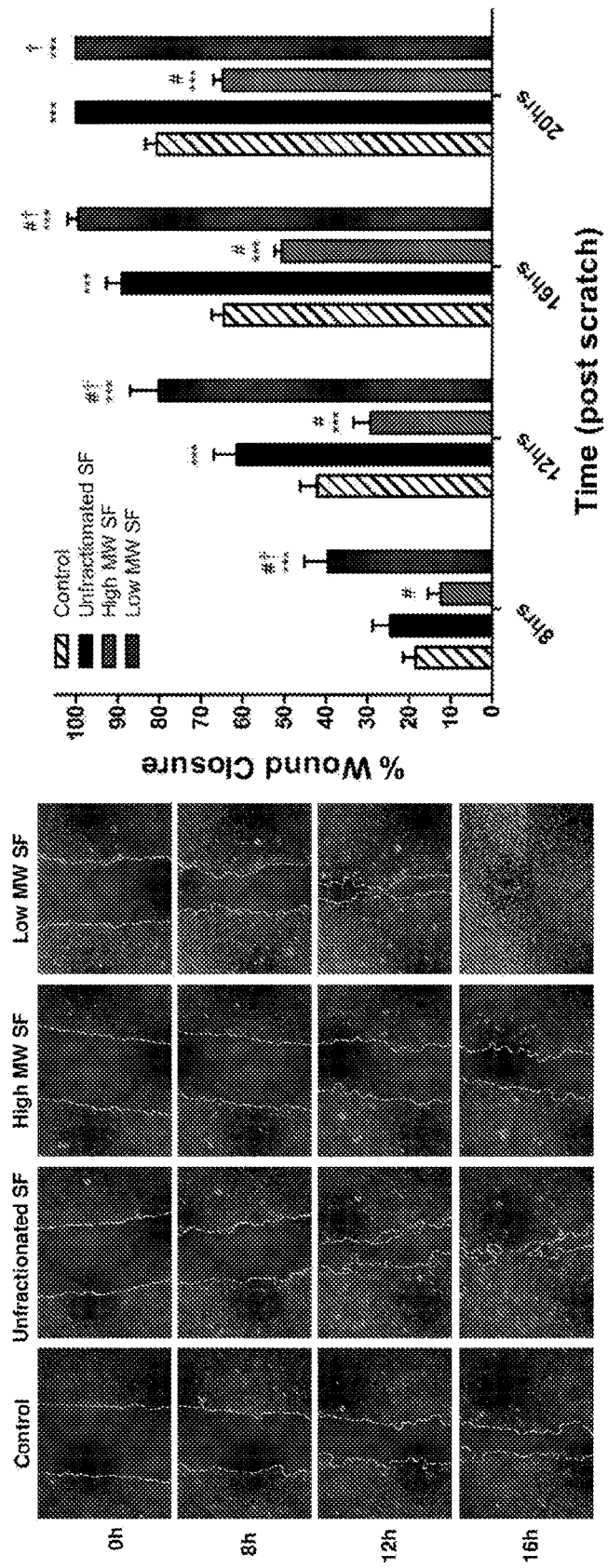
FIG. 8A and FIG. 8B illustrates that low molecular weight SDP fragment enhances scratch wound closure in vitro.

Corneal epithelial cell behavior, during wound healing on the ocular surface, was mimicked in vitro using confluent HCLE cell sheets that were partially denuded to model a corneal abrasion. The cells were subsequently treated in the absence or presence of high and low molecular weight, as well as unfractionated (positive control), SDP solution and the epithelial growth and migration rates were subsequently calculated by measuring cell coverage into the denuded space at defined time points (FIG. 8A). Low molecular weight SDP appears to stimulate wound closure. Treatment with unfractionated SDP, showed a 40% increase in wound closure by 16 hours, relative to control cells. Wound healing rate was further enhanced when cells were treated with low molecular weight SDP, which resulted in an over 50% and 10% increase in wound closure by 16 hours, compared to control cells and cells treated with unfractionated silk, respectively. Similar to previous experiments demonstrating a decrease in epithelial cell migration and growth, treatment with high molecular weight silk unsurprisingly resulted in a significant reduction in scratch closure time as evidenced by a 20% and 50% decrease in wound closure by 16 hours, relative to control cells and cells treated with low molecular weight silk, respectively (FIG. 8B).

Example 8: HCLE Cell Migration

HCLE cells were seeded within 24 well plates (VWR Radnor, Pa., USA), at $1 \times 10^4$ cells/cm$^2$, and allowed to incubate for a 24 hour period in K-SFM media. The K-SFM media was then removed and the cells were treated with fresh K-SFM media containing increasing concentrations (1 mg/mL, 2 mg/mL, and 4 mg/mL) of high molecular weight or low molecular weight SDP protein solution for 20 hours. Cells were treated with fresh K-SFM media containing 4 mg/mL of unfractionated SDP solution or PBS vehicle as a positive control and negative control, respectively. Cell migration was monitored using the microscope's 24-well plate micro-incubator (PeCon, GmbH; M24 S1), a Zeiss Observer Z1 microscope (Carl Zeiss, AG) with 10× objective, 1.6× Opto Var. and phase contrast filter. The microscope's Mark-and-Find feature was used to memorize selected positions within each well to capture multiple areas. Time-lapse phase contrast imaging was utilized to record a frame every 15-minutes over the 20 hour incubation period with an AxioCam single-channel camera and AxioVision software (Carl Zeiss, AG).

Single cell migration and migratory paths of individual HCLE cells, was analyzed using the 'Tracking' package in AxioVision software for individual time-lapse movies. Randomly sampled cells, from each group were tracked from representative locations within each well and the software compiled average measurements for single cell migration rate.

Figure 6:
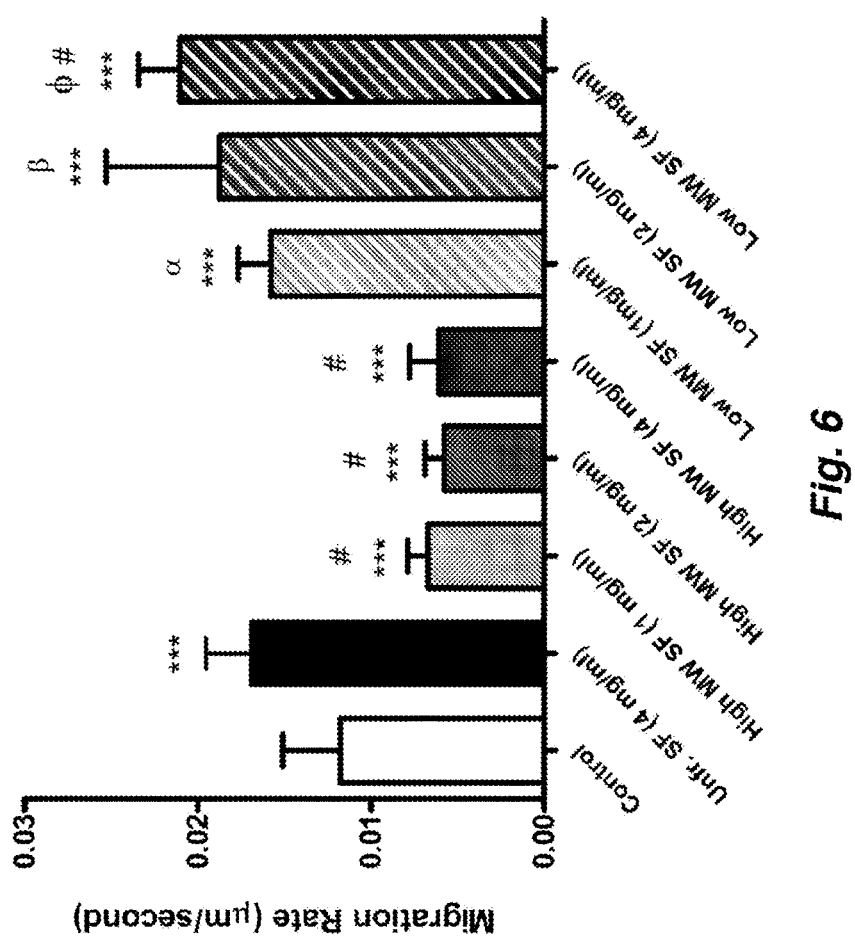
FIG. 6 illustrates that soluble SDP promotes human corneal limbal-epithelial (HCLE) cell migration in vitro. Summary graph showing the mean singular cell migratory rate of HCLE cells treated with increasing concentrations of different MW SDP (Unfr. SF=Unfractionated SDP; High MW SF=High molecular weight SDP; Low MW SF=Low molecular weight SDP) (*** $p<0.05$ vs. Control; #$p<0.05$ vs. Unfr. SF; α $p<0.05$ vs. High MW SF (1 mg/ml); β $p<0.05$ vs. High MW SF (2 mg/ml), φ $p<0.05$ vs. High MW SF (4 mg/ml); N=3, n=100).

HCLE cells were cultured in the absence or presence of increasing concentrations of high and low molecular weight, as well as unfractionated (positive control), SDP solution. The motility of single cells was assessed, utilizing cell tracking software, and the average migration rates of randomly selected cells from each group were compared (FIG. 6). Low molecular weight SDP appears to stimulate epithelial cell migration. As expected, cells treated with 4 mg/mL of unfractionated SDP showed a 40% increase in average cell migration rate, relative to control cells. Interestingly, however, treatment with all concentrations of high molecular weight SDP protein resulted in a 50% decrease in cell migration rate, when compared to control cells, and a 60% decrease in cell migration rate, relative to cells treated with unfractionated silk. Strikingly, treatment with low molecular weight SDP protein demonstrated the opposite effect, evidenced by results showing a dose dependent increase in cell migration rate. Cells treated with 4 mg/mL of low molecular weight SDP protein showed an ~80% and a 20% increase in cell migration rate, relative to cells treated with vehicle control and unfractionated silk, respectively. Additionally, treatment with 4 mg/mL of low molecular weight silk resulted in a 200% increase in cell migration rate relative to cells treated with high molecular weight silk of the same concentration.

Example 9: Epithelial Cell Viability Assay

HCLE cells were cultured in a 96-well plate (VWR Radnor, Pa., USA), at a cell seeding density of $3 \times 10^3$ cells/cm$^2$ in the presence of increasing concentrations (1 mg/mL, 2 mg/mL, and 4 mg/mL) of high molecular weight or low molecular weight SDP protein solution. Cells were treated with 4 mg/mL of unfractionated SDP solution or PBS vehicle as a positive control and negative control, respectively. The cultures were then subjected to the MTT colorimetric assay, following manufacturer instructions, at 12 hours post treatment, which was the duration when the greatest impact of wound healing was observed in vitro, from our previous studies. Briefly, 50 µl of MTT stock solution (5 mg/mL, Gibco, Invitrogen Corporation, Grand Island, N.Y., USA) was added to the cultures containing 500 µl of fresh medium and incubated at 37° C. for 4 hours in the dark. After the medium was aspirated, 200 µl of Dimethyl Sulfoxide (DMSO, Sigma-Aldrich, St. Louis, Mo., USA) was added and mixed thoroughly to release the formazan. The absorbance of the resultant solution was recorded at 540 nm using a Biomek plate reader (Beckman Coulter, Brea, Calif., USA). Wells containing culture media, without cells, were set up as negative controls.

Figure 7:
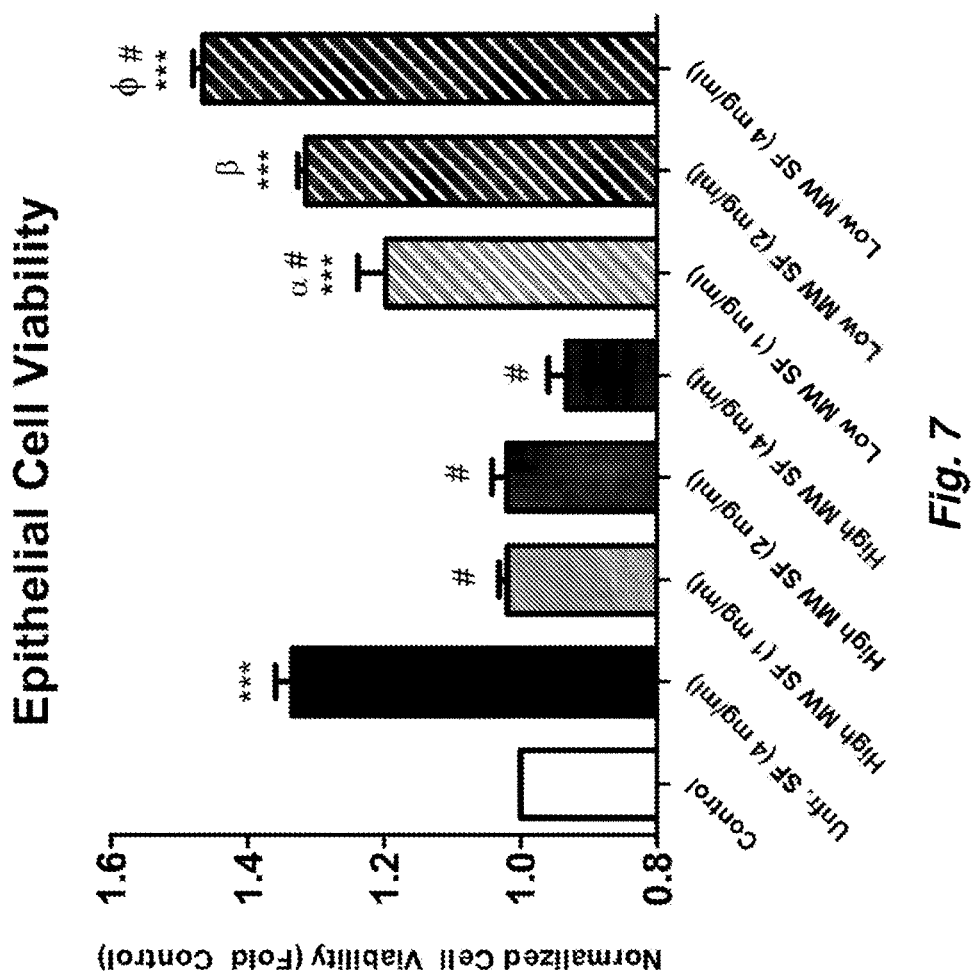
FIG. 7 illustrates that SDP enhances HCLE cell growth and viability in vitro. Summary graph of MTT viability assay performed on cells cultured in the presence of increasing concentrations of different MW SDP solutions for 12 hours. (*** $p<0.05$ vs. Control; #$p<0.05$ vs. Unfr. SF; α $p<0.05$ vs. High MW SF (1 mg/ml); β $p<0.05$ vs. High MW SF (2 mg/ml); φ $p<0.05$ vs. High MW SF (4 mg/ml); N=3, n=3).

Studies were performed to evaluate whether molecular weight also plays a role in influencing SDP's effects on epithelial cell proliferation. HCLE cells were cultured in like numbers in the absence or presence of increasing concentrations of high and low molecular weight, as well as unfractionated (positive control), SDP solution for 12 hours, which was the duration during which the greatest increase in wound healing was observed in vitro, during our previous studies. The cultures were then subjected to an MTT colorimetric metabolic assay to evaluate the difference in cell number (FIG. 7). Low molecular weight SDP stimulates epithelial cell proliferation. Corroborating results from our previous research efforts, treatment with 4 mg/mL of unfractionated silk enhanced cell proliferation by over 30%, relative to control cells. Surprisingly, cells treated with all concentrations of high molecular weight SDP did not show any increase or decrease in cell proliferation, relative to control cells. However, cell proliferation was significantly increased in a dose dependent manner when cells were treated with low molecular weight SDP. Cells treated with 4 mg/mL of low molecular weight SDP solution, showed a 45% and 10% enhancement in cell growth, relative to control cells and cells treated with unfractionated silk, respectively. Moreover, cell proliferation was over 50% higher when compared to cells treated with high molecular weight SDP.

Example 10: Cell Substrate Adhesion Assay

HCLE cells were seeded in 35 mm cell culture dishes, at $3 \times 10^5$ cells per dish. This cell seeding density was chosen to ensure proper surface coverage with minimal cell-cell contact formation. Cells were allowed to incubate overnight to ensure optimal cell attachment to the substrate.

Media from the cell-seeded dishes was removed and fresh K-SFM with 4 mg/mL of different SDP protein solutions (high molecular weight, low molecular weight, or unfractionated) or PBS vehicle control was added, and the cells were allowed to incubate overnight. Following incubation, cell substrate adhesion was evaluated using a parallel plate flow chamber cell (Glycotech, Gaithersburg, Md.). The flow channel within the chamber had dimensions of 5 mm width (w), 0.1 mm height (h), and 48.2 mm length (1). Media was aspirated from the cell-seeded dishes and the flow chamber was placed on top of the cells. PBS was warmed to 37° C. to yield an apparent fluid viscosity (μ) of ~0.8 cp. A syringe pump was used to deliver the PBS at a volumetric flow rate (Q) of 52.2 ml/min to create a continuous one dimensional laminar fluid flow within the channel. The wall shear stress was determined as previously described. The delivered fluid shear stress is defined by the following equation:

$$\tau w = 6\mu Q/b(h^2)$$

The channel width (b) and channel height (h) are fixed variables dictated by the dimensions of the silicone gasket attached to the flow chamber deck, placed over the cells. PBS that is infused through the flow channel to create laminar flow conditions is kept at 37° C. to yield a constant apparent fluid viscosity (μ) of ~0.8 cp throughout the course of the assay. Thus, the delivered wall shear stress (τw) remains solely a function of the volumetric flow rate (Q) of the PBS infused by the syringe pump. Cells were subjected to a wall shear stress of 98.4 Pa for 1 minute, and areas of analysis, with a cell count of 30-40 cells, were imaged during the course of the assay on a Zeiss Observer Z1 microscope (Carl Zeiss, AG) with 10× objective and phase contrast filter.

Images of the cells were captured using an AxioCam single-channel camera and AxioVision software (Carl Zeiss, AG). The total number of adherent cells within the area of analysis was determined before and after the onset of flow. Cellular adhesion of cells treated with different SDP protein solutions was evaluated and compared to cells treated with PBS buffer (treatment vehicle) as a control.

Figure 9:
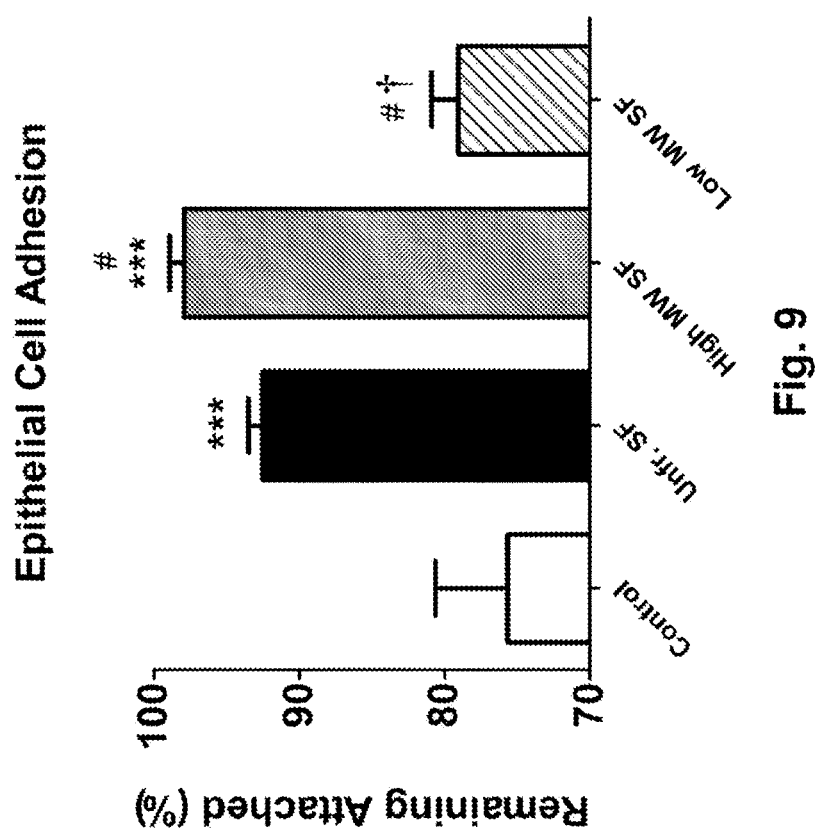
FIG. 9 illustrates a summary graph demonstrating a significant increase in the number of remaining adhered HCLE cells after exposure to high fluid shear forces, indicating an enhancement in cell-substrate adhesive strength when cells were treated with high MW SDP. (*** $p<0.05$ vs. Control; #$p<0.05$ vs. Unfr. SF; † $p<0.05$ vs. High MW SF; N=3, n=100).

HCLE cells were cultured in the absence or presence of high and low molecular weight, as well as unfractionated, SDP solution and a laminar fluid flow chamber was utilized to evaluate and quantify the resistance of the cells to detachment when challenged by fluid shear, as previously described (FIG. 9). High molecular weight SDP appears to promote epithelial cell-substrate adhesion through organization of focal adhesion complexes and re-alignment of epithelial cell cytoskeleton. When challenged with continuous, one dimensional, fluid shear, non-fibroin treated (control) cell retention was approximately 75%. Expectedly, the addition of 4 mg/mL of unfractionated SDP significantly increased cell retention to over 90%.

Interestingly, cell retention was further increased by 5% when cells were treated with high molecular weight SDP, indicating an improvement in cell-matrix adhesion. Intriguingly, however, cell attachment was not improved by the addition of low molecular weight SDP as evidenced by a 14% and 18% decrease in cell retention, relative to unfractionated silk and high molecular weight silk treated cells, respectively. Furthermore, the cell detachment profile and the cell retention of low molecular weight silk treated cells upon being subjected to high shear, was not statistically different to that of control cells.

Example 11: HCLE Immunofluorescent Staining and Imaging

HCLE cells were cultured overnight in the presence of 4 mg/mL of different SDP protein solutions (high molecular weight, low molecular weight, or unfractionated) or PBS vehicle control, were fixed with 4% paraformaldehyde (PFA, Electron Microscopy Sciences, Hatfield, Pa., USA) for 15 minutes, then rehydrated in PBS containing 0.5% bovine serum albumin (BSA, Sigma-Aldrich, St. Louis, Mo., USA), and 0.05% nonionic surfactant (Triton-X-100; Sigma-Aldrich, St. Louis, Mo., USA) for 1 hour. After fixation, 50 μl of primary antibody solution (anti-vinculin, 1:400, Sigma-Aldrich, St. Louis, Mo., USA) were added for 1 hour at room temperature. Samples were incubated with secondary antibody for 1 hour using appropriate isotype matched non-specific IgG as controls. Samples were also stained with Alexa Fluor® 568 phalloidin (Gibco, Invitrogen Corporation, Grand Island, N.Y., USA). After washing with PBS, Samples were mounted with VECTASHIELD Mounting Medium with DAPI (Vector Laboratories, Burlingame, Calif., USA). Fluorescent staining was visualized using Observer Z1 fluorescent microscope (Carl Zeiss, AG) with both 10× and 40× objective lenses. An AxioCam HRm digital camera (Carl Zeiss, AG) and AxioVision 4.0 software were used to capture single and z-stack images (45-60 layer range) at 0.25 μm slices using DAPI, GFP, and Texas Red filter channels. Deconvolution was performed on each z-stack using 3D Huygens Deconvolution Software (Scientific Volume Imaging BV, The Netherlands).

Figure 10:
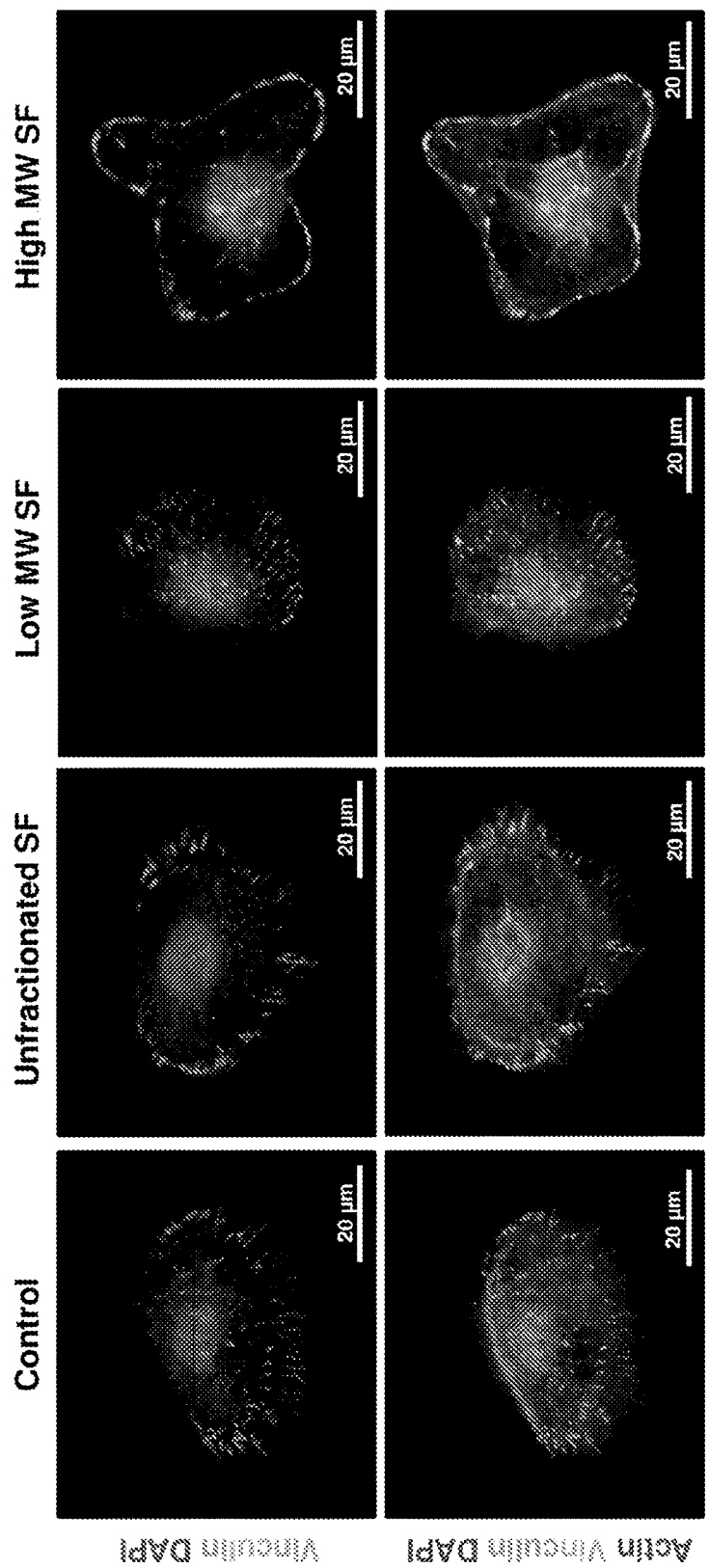
FIG. 10 illustrates that SDP enhances cell adhesion by promoting focal adhesion clustering. Representative images of HCLE cells cultured in PBS treatment vehicle (control) and in the presence of unfractionated SF (positive control), low MW SF, or high MW SF. Cells treated with unfractionated or High MW SF exhibited increased vinculin (green) staining along the cell membrane, indicating points of cell attachment (nucleus=blue). Vinculin clustering along the periphery of the cell was more pronounced with high MW SF treatment, relative to all other treatment groups.

Immunofluorescent staining and imaging of vinculin was used to visualize and assess the formation and arrangement of focal adhesion subunits in HCLE cells cultured in the presence or absence of high and low molecular weight, as well as unfractionated, SDP solution (FIG. 10). Treatment with PBS vehicle (control) and low molecular weight silk resulted in a dispersed arrangement of vinculin along the basal plasma membrane surface. In contrast, however, clustering and aggregation of vinculin along the cell periphery occurred in unfractionated silk treated cells, and significantly increased when cells were treated with high molecular weight silk, which was shown to enhance cell adhesion the most during the previous experiment.

Example 12: Cell Spreading and Cytoskeleton Re-Organization

HCLE cells cultured overnight in the presence of 4 mg/mL of different SDP protein solutions (high molecular weight, low molecular weight, or unfractionated) or PBS vehicle control, were fixed with 4% paraformaldehyde (PFA, Electron Microscopy Sciences, Hatfield, Pa., USA) for 15 minutes, then rehydrated in PBS containing 0.5% BSA (Sigma-Aldrich, St. Louis, Mo., USA), and 0.05% Triton-X-100 (Sigma-Aldrich, St. Louis, Mo., USA) for 1 hour. After fixation, samples were stained with Alexa Fluor® 568 phalloidin (1:40, Gibco, Invitrogen Corporation, Grand Island, N.Y., USA) for 20 minutes. After washing with PBS, samples were mounted with VECTASHIELD Mounting Medium with DAPI (Vector Laboratories, Burlingame, Calif., USA). Fluorescent staining was visualized using Observer Z1 fluorescent microscope (Carl Zeiss, AG) with a 10× objective lens. An AxioCam HRm digital camera (Carl Zeiss, AG) and AxioVision 4.0 software were used to capture single and z-stack images (45-60 layer range) at 0.25 µm slices using DAPI and Texas Red filter channels. Deconvolution was performed on each z-stack using 3D Huygens Deconvolution Software (Scientific Volume Imaging BV, The Netherlands). The surface area of the cells, under both sparse and confluent conditions were measured using ImageJ software (ver. 1.48, NIH) to evaluate alterations to cell spreading in response to stimulation by different SDP fractions.

To determine whether alterations to the cell cytoplasm had occurred in response to treatment with SDP solutions of different molecular weights, HCLE cells were plated on 2-dimensional surfaces at a low density to mimic environments adjacent to a wound area, or at a high density to form a confluent intact monolayer as would exist on the healthy ocular surface, and subsequently treated with PBS vehicle (control) or high and low molecular weight, as well as unfractionated, SDP solution. The cell surface area of the treated cells was then measured to evaluate cell spreading (FIGS. 11A and 11B). Cells that were in compact cell sheets, possessed a lower average surface area when compared to cells cultured at lower densities, which had more room for spreading. However, incubation with unfractionated SDP stimulated a robust increase in cell surface area, for both low and high cell densities, and the degree of cell spreading was further increased when cells were treated with high molecular weight silk. Interestingly, the observed cell response was molecular weight dependent, as treatment with low molecular weight silk did not result in any significant increases in cell spreading when compared to non-fibroin treated (control) cells.

Example 13: RNA Isolation and Quantitative PCR

HCLE cells were seeded in 35 mm dishes at $6 \times 10^5$ cells per dish and cultured for 12 hours in the presence of 4 mg/mL of different SDP protein solutions (high molecular weight, low molecular weight, or unfractionated) or PBS vehicle control. Total RNA was then extracted using Qiagen RNeasy Plus Mini Kit (Qiagen, Valencia, Calif., USA), and RNA integrity and quantity were checked using Agilent Technologies 2100 Bioanalyzer and Nanodrop Spectrophotometer at the Genomics Resources Core Facility of Weill Cornell Medical College. Afterwards, 450 ng of total RNA from each sample was reverse transcribed into cDNA using the High Capacity cDNA Reverse Transcription kit (Applied Biosystems, Life Technologies, Grand Island, N.Y.). Quantitative PCR was carried out in a Step One Plus real time PCR system (Applied Biosystems, Life Technologies, Grand Island, N.Y.) using the SYBR Select Master Mix kit (Applied Biosystems, Life Technologies, Grand Island, N.Y.) and the following specific primer sets:

| | | |
|---|---|---|
| hTGFA-Fw: | TTTTGGTGCAGGAGGACAAG | (SEQ ID NO: 1) |
| hTGFA-Rv: | GCACACATGTGATGATAAGG | (SEQ ID NO: 2) |
| hTGFB1 Fw: | AATGGTGGAAACCCACAACG | (SEQ ID NO: 3) |
| hTGFB1-Rv: | GCTGCTCCACTTTTAACTTG | (SEQ ID NO: 4) |
| hTGFB2 Fw: | GTTCAGAGTCTTTCGTTTGC | (SEQ ID NO: 5) |
| hTGFB2-Rv: | TCAGTTACATCGAAGGAGAG | (SEQ ID NO: 6) |
| hTGFB3-Fw: | ATGAGCACATTGCCAAACAG | (SEQ ID NO: 7) |
| hTGFB3-Rv: | GGACAGTGAATGCTGATTTC | (SEQ ID NO: 8) |

The expression of candidate genes was normalized against the housekeeping gene, glyceraldehyde-3-phosphate-dehydrogenase (GAPDH). Relative quantitation was performed using the $2^{(-\Delta\Delta Ct)}$ method.

Example 14: Role of TGFβ Signaling in SDP Induced Wound Closure

To evaluate the possible involvement of TGFβ signaling in SDP induced wound closure, TGFβRI specific inhibitor (5 µM, SB431542, Tocris Bioscience, Ellisville, Mo.) was used to inhibit the TGFβ signaling pathway in HCLE cells during wound closure. HCLE cells were seeded within 24 well plates (VWR Radnor, Pa., USA), at $5 \times 10^4$ cells/cm², and allowed to incubate for a 24 hour period in K-SFM media to form a confluent monolayer of cells. A scratch assay was then performed as described previously in the presence low molecular weight SDP protein solution or PBS vehicle, with or without 5 µM of TGFβRI specific inhibitor SB431542, to elucidate the role of TGFβ mediated signaling during SDP induced cell migration and acceleration of wound healing. A two-way ANOVA test was performed to reveal whether any of the experimental groups were affected by the differences in molecular weight of SDP and to identify statistically significant changes in cellular responses between different treatment groups and control groups. P values were calculated using Prism Software.

Figure 12:
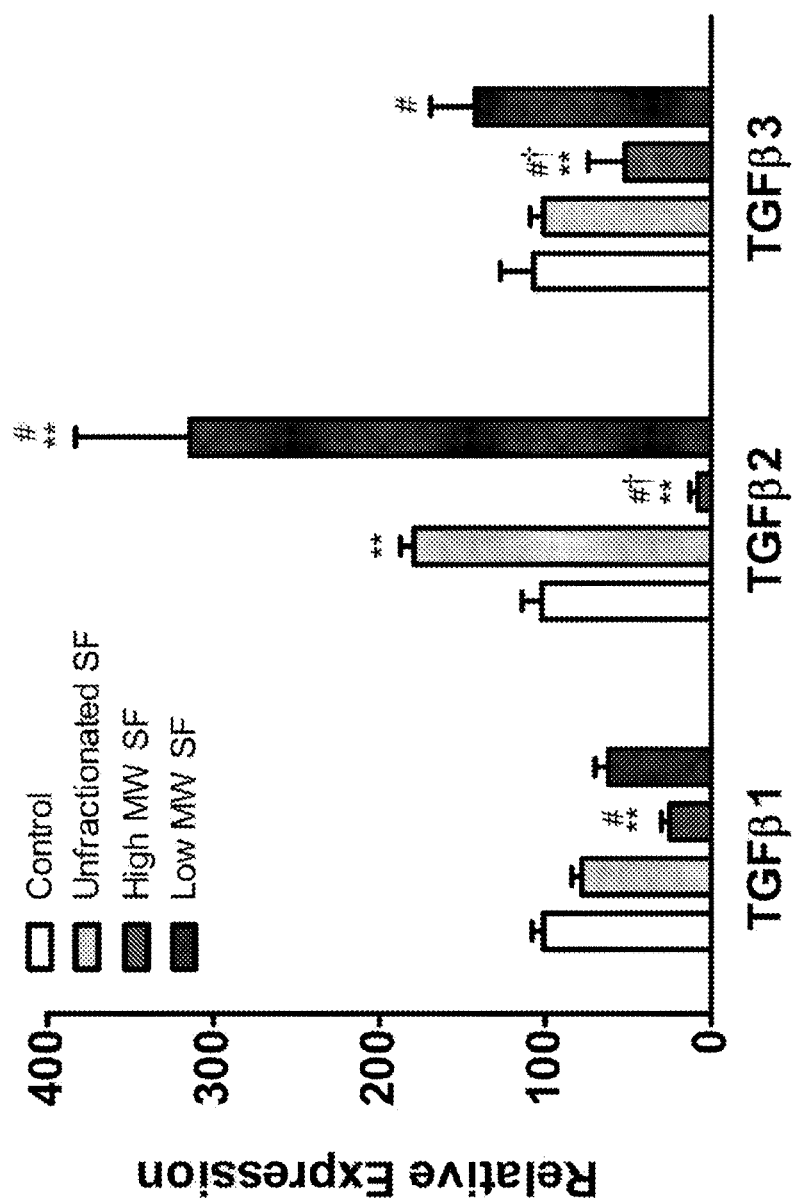
FIG. 12 illustrates Q-PCR of relative expression of the TGFβ family of genes in HCLE cells cultured in the presence of different MW SDP solutions, or PBS vehicle treatment (control). (** $p<0.05$ vs. Control; # $p<0.05$ vs. Unfr. SF; † $p<0.05$ vs. Low MW SF; N=3, n=100).

QPCR was performed and the genetic expression of TGFβ1, TGFβ2, and TGFβ3 was analyzed (FIG. 12). SDP appears to influence TGFβ genetic expression. Treatment with low molecular weight SDP evoked over a 2 fold increase and a 1.75 fold increase in TGFβ2 gene expression relative to non-fibroin treated (control) cells and cells treated with unfractionated silk, respectively. Treatment with either unfractionated silk or low molecular silk did not result in significant changes of TGFβ1 gene expression, while TGFβ3 gene expression was significantly increased with low molecular weight silk. Additionally, the molecular weight dependence of SDP's stimulatory effects was further exemplified by the significant decrease in genetic expression of all genes when cells were treated with high molecular weight silk.

Figures 13A, 13B:
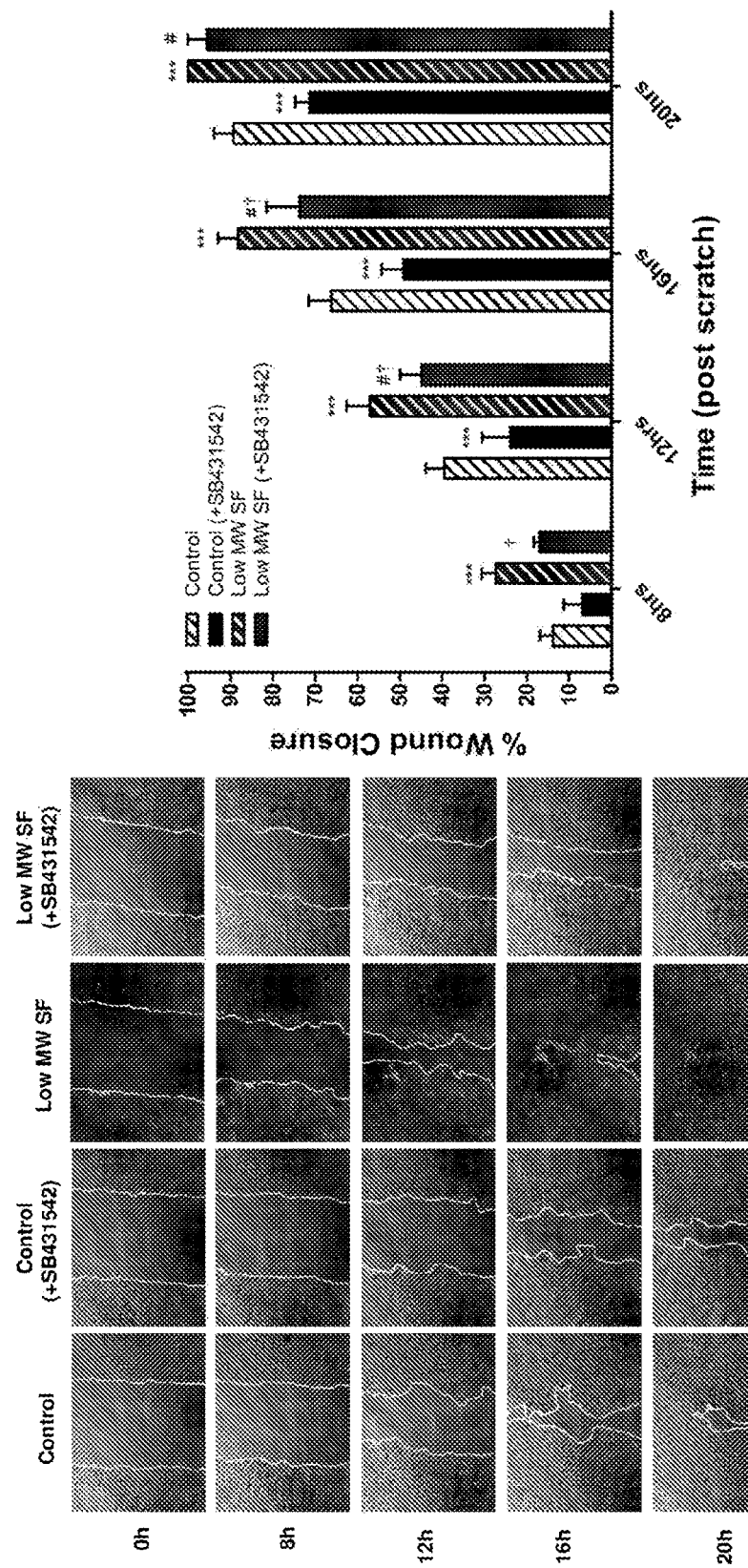
FIG. 13A and FIG. 13B illustrate the effects of low molecular weight silk on cell migration and scratch wound closure in vitro are attenuated in the presence of a TGFβ signaling pathway inhibitor.

A scratch assay was performed using HCLE cells treated with PBS vehicle (control) or low molecular weight SDP, in the presence or absence of 5 µM of TGFβRI specific inhibitor, SB431542. TGFβ signaling pathway inhibitor appears to prevent low molecular weight SDP induced cell migration and wound closure. Results demonstrate that low molecular weight SDP stimulation of cell migration was attenuated by inhibition of TGFβ signaling (FIGS. 13A and 13B). Cells treated with low molecular weight silk in the presence of SB431542 showed a significant decrease in healing rate and an ~20% decrease in wound closure by 16 hours, relative to cells treated with low molecular weight silk without SB431542. It is important to note that the addition of SB431542 to non-fibroin treated cells also reduced cell migration and wound closure rate relative to non-fibroin treated cells without SB431542.

Example 15

A sample of a wound treatment composition is prepared. Protein fragments are isolated from a silk-derived fibroin protein composition according to molecular weight. A first hydrolysate of protein fragments of low molecular weight, such as less than about 60 kDa, is formed. A second hydrolysate of protein fragments of high molecular weight, such as greater than about 60 kDa, is formed. A third hydrolysate of protein fragments is formed from the first hydrolysate and second hydrolysate for a mixture of protein fragments of less than about 60 kDa and greater than about 60 kDa. Each hydrolysate includes water, at least one buffer system (e.g. PBS, citrate, borate), at least one preservative, at least one additional excipient (stabilizers, salts).

The first hydrolysate is applied to a surgical wound of a healthy patient (e.g. post refractive surgery). The wound is monitored over time for wound closure rate and patient comfort and pain assessment.

The second hydrolysate is applied to a chronic wound, diabetic ulcer, or burn wound. The wound is monitored for wound closure.

The third hydrolysate is applied to any wound. The wound is monitored for wound closure rate and quality.

In accordance with 35 U.S.C. 102(c), (1) the subject matter disclosed was developed and the claimed invention was made by, or on behalf of, the parties to a joint research agreement that was in effect on or before the effective filing date of the claimed invention; (2) the claimed invention was made as a result of activities undertaken within the scope of the joint research agreement; and (3) the names of the parties to the joint research agreement are (a) Silk Technologies, Ltd. and (b) Cornell University. The inventors have assigned their rights in the invention to Silk Technologies, Ltd. or Cornell University.

What is claimed is:

1. A method for treating an ocular wound comprising:
applying a composition of silk fibroin-derived protein (SDP) fragments to living animal tissue in the ocular wound;
wherein a primary amino acid sequences of the SDP fragments differs from native silk fibroin by at least 4% with respect to the combined amino acid content of serine, glycine, and alanine;
the SDP fragments that have a serine content that is reduced by greater than 40% compared to native silk fibroin, wherein the serine content is at least about 5%;
wherein the SDP fragments are derived from silkworm silk, spider silk, or genetically engineered silk, and having an average molecular weight between about 30 kDa and 60 kDa, and
wherein a plurality of the SDP fragments terminate in amide (—C(=O)NH$_2$) groups, thereby treating the ocular wound.

2. The method of claim 1, wherein cysteine disulfide bonds between the silk fibroin heavy and silk fibroin light protein chains of fibroin are reduced or eliminated.

3. The method of claim 1, wherein the composition possesses enhanced stability in an aqueous solution compared to native silk fibroin.

4. The method of claim 1, wherein the SDP protein fragments are derived from *Bombyx mori*.

5. The method of claim 1, wherein at least 75 percent of the SDP fragments have a molecular weight of less than about 100 kDa.

6. The method of claim 1, wherein at least 90 percent of the SDP fragments have a molecular weight of less than about 100 kDa.

7. The method of claim 1, wherein at least 75 percent of the protein fragments have a molecular weight between about 30 kDa and 60 kDa.

8. The method of claim 1, wherein at least 90 percent of the protein fragments have a molecular weight between about 30 kDa and 60 kDa.

9. The method of claim 1, wherein at least 50 percent of the protein fragments have a molecular weight of greater than about 60 kDa.

10. The method of claim 1, wherein the SDP fragments promote cell migration and proliferation in the tissue to close the wound.

11. The method of claim 1, wherein the ocular wound is caused by an ocular condition, and wherein the ocular condition is corneal ulcer, corneal erosion, corneal abrasion, corneal degeneration, corneal perforation, corneal scarring, epithelial defect, keratoconjunctivitis, idiopathic uveitis, corneal transplantation, dry eye syndrome, age-related macular degeneration, diabetic eye, blepharitis, glaucoma, ocular hypertension, post-operative eye pain and inflammation, posterior segment neovascularization, proliferative vitreoretinopathy, cytomegalovirus retinitis, endophthalmitis, choroidal neovascular membrane, vascular occlusive disease, allergic eye disease, tumor, retinitis pigmentosa, eye infection, scleritis, ptosis, miosis, eye pain, mydriasis, neuralgia, cicatrizing ocular surface disease, ocular infection, inflammatory ocular disease, ocular surface disease, corneal disease, retinal disease, ocular manifestations of systemic diseases, hereditary eye condition, ocular tumor, increased intraocular pressure, herpetic infection, ptyrigium or scleral tumor, wound sustained to ocular surface, post-photorefractive keratotomy eye pain and inflammation, thermal or chemical burn to the cornea, scleral wound, or keratoconus and conjunctival wound.

12. The method of claim 1, wherein the composition further comprises a pharmaceutical carrier and the composition is formulated as an aqueous solution, a suspension, a dispersion, a salve, an ointment, a gel, a cream, a lotion, a spray, or a paste.

* * * * *